US 11,045,810 B2

(12) United States Patent
Dority

(10) Patent No.: US 11,045,810 B2
(45) Date of Patent: Jun. 29, 2021

(54) THERMAL CYCLING METHODS

(71) Applicant: Cepheid, Sunnyvale, CA (US)

(72) Inventor: Doug Dority, Mill Valley, CA (US)

(73) Assignee: Cepheid, Sunnyvale, CA (US)

(*) Notice: Subject to any disclaimer, the term of this patent is extended or adjusted under 35 U.S.C. 154(b) by 360 days.

(21) Appl. No.: 15/887,248

(22) Filed: Feb. 2, 2018

(65) Prior Publication Data

US 2018/0169659 A1 Jun. 21, 2018

Related U.S. Application Data

(62) Division of application No. 14/396,029, filed as application No. PCT/US2013/041231 on May 15, 2013, now Pat. No. 9,908,119.

(60) Provisional application No. 61/647,493, filed on May 15, 2012.

(51) Int. Cl.
*B01L 7/00* (2006.01)
*B01L 7/02* (2006.01)
*C12P 19/34* (2006.01)
*B01L 3/00* (2006.01)

(52) U.S. Cl.
CPC .............. *B01L 7/52* (2013.01); *B01L 7/02* (2013.01); *C12P 19/34* (2013.01); *B01L 3/502715* (2013.01); *B01L 2300/0809* (2013.01); *B01L 2300/0816* (2013.01); *B01L 2300/1827* (2013.01); *B01L 2300/1844* (2013.01); *B01L 2300/1894* (2013.01)

(58) Field of Classification Search
None
See application file for complete search history.

(56) References Cited

U.S. PATENT DOCUMENTS

| 5,187,084 | A | 2/1993 | Hallsby |
| 5,333,675 | A | 8/1994 | Mullis et al. |
| 5,942,432 | A | 8/1999 | Smith et al. |
| 6,238,913 | B1 | 5/2001 | Buckner, III |
| 6,372,486 | B1 | 4/2002 | Fripp |
| 6,482,615 | B2 | 11/2002 | Tal et al. |
| 6,521,447 | B2 | 2/2003 | Zou et al. |
| 6,586,233 | B2 | 7/2003 | Benett et al. |
| 7,411,792 | B2 | 8/2008 | Richards et al. |
| 7,537,377 | B2 | 5/2009 | Atwood et al. |
| 7,858,365 | B2 | 12/2010 | Fawcett |
| 9,908,119 | B2 | 3/2018 | Dority |

(Continued)

FOREIGN PATENT DOCUMENTS

| EP | 1710017 | 11/2006 |
| JP | H03-096831 A | 4/1991 |

(Continued)

OTHER PUBLICATIONS

Schmoldt, Alexander, "High performance cooling in small spaces," Components in Electronics, Mar. 2010, pp. 20-21, http://www.cieonline.co.uk.

(Continued)

*Primary Examiner* — Samuel C Woolwine
(74) *Attorney, Agent, or Firm* — Kilpatrick Townsend & Stockton LLP

(57) ABSTRACT

A thermal cycling apparatus having a sample interfacing wall extending from a mounting wall. The sample interfacing wall can accept and apply thermal cycles to samples. An air source can direct an air stream to cool the sample. Another source can direct heated air away from the sample.

19 Claims, 22 Drawing Sheets

(56) References Cited

U.S. PATENT DOCUMENTS

| | | |
|---|---|---|
| 2002/0006619 A1 | 1/2002 | Cohen et al. |
| 2004/0265892 A1 | 12/2004 | Wittwer et al. |
| 2007/0257766 A1 | 11/2007 | Richards et al. |
| 2008/0038163 A1 | 2/2008 | Boege et al. |
| 2008/0050781 A1 | 2/2008 | Oldham et al. |
| 2009/0087903 A1 | 4/2009 | Belgrader et al. |
| 2010/0233763 A1 | 9/2010 | Shigeura et al. |

FOREIGN PATENT DOCUMENTS

| | | |
|---|---|---|
| JP | H03-128432 A | 5/1991 |
| JP | 2008221213 A | 9/2008 |
| WO | 1998/038487 A2 | 9/1998 |
| WO | 2004/054716 A1 | 7/2004 |
| WO | 2004/056485 A1 | 7/2004 |
| WO | 2005/058501 A1 | 6/2005 |
| WO | 2006/105919 A1 | 12/2006 |
| WO | 2007/149696 A1 | 12/2007 |

OTHER PUBLICATIONS

Shaw, Kirsty J. et al., "Rapid PCR Amplification using a Microfluidic Device with Integrated Microwave Heating and Air Impingement Cooling," Lab on a Chip, 2010, Issue 10, pp. 1725-1728.
Qiu, Xianbo et al., "A large volume, portable, real-time PCR reactor," Lab on a Chip, 2010, Issue 10, pp. 3170-3177.
International Search Report and Written Opinion dated Sep. 12, 2013, from PCT Application No. PCT/US2013/041231 (12 pages).
Extended European Search Report in EP13790994.1, dated Dec. 1, 2015, 7 pages.
International Preliminary Report on Patentability dated Nov. 27, 2014 in PCT/US2013/041231, 8 pages.

(AIR SOURCE REMOVED TO SHOW CONNECTOR 212)

THERMAL CYCLING METHODS

BACKGROUND OF THE INVENTION

This application is a Divisional of U.S. application Ser. No. 14/396,029, filed Oct. 21, 2014 (now U.S. Pat. No. 9,908,119), which is a U.S. National Phase of International Application No. PCT/US2013/041231, filed May 15, 2013, which claims priority to U.S. Provisional Patent Application No. 61/647,493, filed on May 15, 2012, the disclosures of which are incorporated by reference.

Various biological testing procedures require thermal cycling, generally to cause a chemical reaction via heat exchange. One example of such a procedure is polymerase chain reaction (PCR) for DNA amplification. Further examples include isothermal nucleic acid amplification, rapid-PCR, ligase chain reaction (LCR), self-sustained sequence replication, enzyme kinetic studies, homogeneous ligand binding assays, and more complex biochemical mechanistic studies that require complex temperature changes.

Such procedures require a testing system that can accurately raise and lower sample temperatures with precision, and in some cases rapidity. Many such systems exist, which typically use cooling devices (e.g., fans) that occupy a large amount physical space and require significant power to provide a required amount of performance (i.e., a rapid temperature drop). Further, such cooling devices have issues with start-up lag time and shut-down overlap, that is, will function after being shut off, and thus do not operate with instantaneous digital-like precision. For example, a centrifugal fan will not instantly blow at full volumetric capability when turned on and will also continue to rotate after power is shut off, thus implementing overlap time that must be accounted for in testing. Such issues typically get worse with device age.

The low cost of such cooling devices, relatively acceptable performance, and easy implementation has prevented industry from answering these issues. The answer thus far, has been to incorporate more powerful fans having greater volumetric output rates, which also increase space and power requirements. One price of this is a negative effect on portability of field testing systems, which can be used, for example, to rapidly detect viral outbreaks in outlying areas. Accordingly, there is an unanswered need to address the deficiencies of known cooling devices used in biological testing systems.

BRIEF SUMMARY OF THE INVENTION

One embodiment of the invention relates to a thermal cycling apparatus that may include a mounting wall partially defining a chamber for thermally cycling biological samples. The mounting wall may have a first mounting surface opposing a second mounting surface. A sample interfacing wall can transversely extend from the second mounting surface. The sample interfacing wall may have a planar interface accessible from the second mounting surface. The sample interfacing wall may include a first heating element and a second heating element on opposing sides of the planar interface. A first air source can have an exit arranged to direct air at the first heating element. A second air source can have an exit arranged to direct air away from the first heating element. A third air source can have an exit arranged to direct air away from the second heating element. A fourth air source can have an exit arranged to direct at the second heating element.

In some embodiments, each air source includes an air pump having a planar face, the exit being on the planar face, and a plurality of edges surrounding the planar face.

In some embodiments, each air pump may be coupled to the second mounting surface such that its planar face is substantially transverse to the second mounting surface.

In some embodiments, the first air pump, second air pump, and sample interfacing wall may be arranged to define a first sub-volume of the chamber.

In some embodiments, the exit of the second air pump can be arranged to push air out of an exit of the first sub-volume.

In some embodiments, the third air pump, fourth air pump, and sample interfacing wall can be arranged to define a second sub-volume of the chamber.

In some embodiments, the exit of the third air pump can be arranged to push air out of an exit of the second sub-volume.

In some embodiments, the first and fourth air sources can be each arranged to direct respective air streams directly at the first and second heating elements.

In some embodiments, the second and third air sources can be each arranged to direct an air stream at the sample interfacing wall.

In some embodiments, the second and third air sources can be each arranged to direct an air stream along the sample interfacing wall.

In some embodiments, the second and third air sources are each arranged to suction air away from the sample interfacing wall.

In some embodiments, the mounting wall and sample interfacing wall can include printed circuit boards.

In some embodiments, the sample interfacing wall can divide the chamber into substantially equal volumes.

In some embodiments, the air sources can be symmetrically positioned about the sample interfacing wall.

In some embodiments, each air source can include a planar housing having an internal piezoelectric element mounted to an internal diaphragm.

In some embodiments, each planar housing can include an exit port, and the exit ports of the first and fourth air sources can be arranged to directly provide respective air streams at the first and second heating elements.

In some embodiments, the exit ports of the second and third air sources can be arranged to provide respective air streams along or away from the sample interfacing wall.

Another embodiment of the invention relates to a thermal cycling method. In the method, a first heating element and a second heating element can be activated, each heating element being positioned adjacent to a biological sample holder. Using a first air source, a first air stream can be directed at a first heating element to transfer heat from the first heating element. Using a second air source, a second air stream can direct heated air away from the first heating element. Using a fourth air source, a fourth air stream can be directed at a second heating element to transfer heat from the second heating element. Using a third air source, a third air stream can direct heated air away from the second heating element.

In some embodiments, the first and second heating elements are positioned on opposed sides of a sample interfacing wall, and the sample interfacing wall may extend from a mounting surface.

In some embodiments, the air sources each can include substantially planar housings edge mounted to the mounting surface.

In some embodiments, the first and fourth air streams can directly intersect the first and second heating elements.

In some embodiments, the second and third air streams can be directed along the sample interfacing wall.

In some embodiments, the second and third air streams can be directed away from the sample interfacing wall.

In some embodiments, each air source can include a planar housing having an internal piezoelectric element mounted to an internal diaphragm.

In some embodiments, each air stream can be directed by powering each piezoelectric element.

In some embodiments, the piezoelectric elements can be powered ON and OFF according to a predetermined cooling cycle.

In some embodiments, the heating elements can be powered ON and OFF according to a predetermined heating cycle, with the ON portion of the heating cycle being out of phase with the ON portion of the cooling cycle.

In some embodiments, temperatures of the first and second heating elements may be monitored.

In some embodiments, the first and second heating elements can be activated to provide heat to the biological sample holder according to a predetermined minimum temperature and a predetermined maximum temperature.

In some embodiments, the air sources may be controlled to direct air when the biological sample holder reaches the predetermined maximum temperature.

In some embodiments, the air sources are controlled to stop directing air when the biological sample holder reaches the predetermined minimum temperature.

BRIEF DESCRIPTION OF THE DRAWINGS

FIG. 5E is a simplified rear view of a variation of the thermal cycling device of FIG. 2A, having pluralities of linked pressurized air sources, in use, according to some embodiment of the invention.

DETAILED DESCRIPTION OF THE INVENTION

Figure 1A:
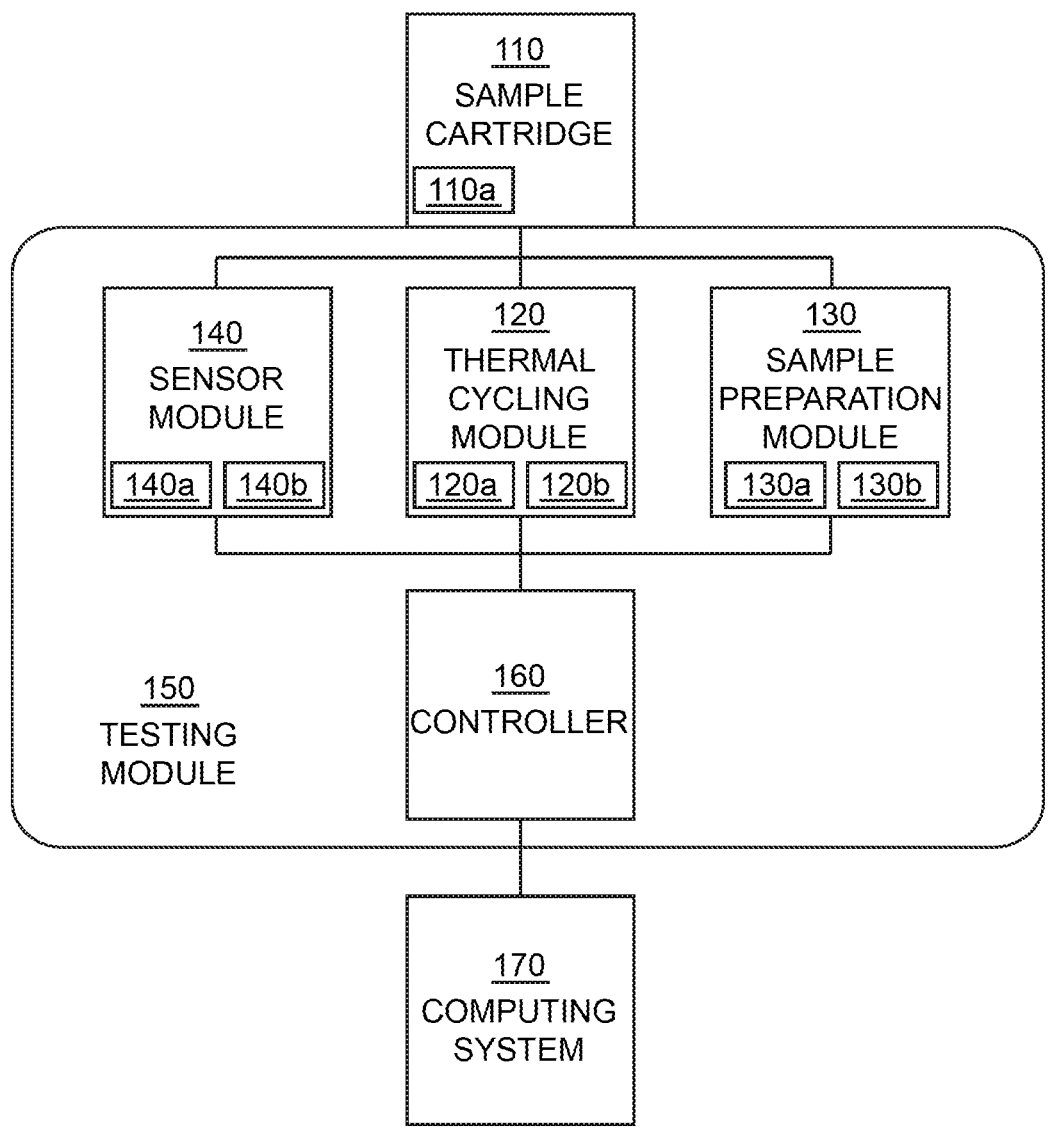
FIG. 1A is a simplified schematic drawing of a testing system 100, according to some embodiments of the invention.

I. System Overview:

FIG. 1 shows a simplified schematic drawing of a system 100 for testing a sample. The system 100 includes a sample cartridge 110, which is configured for receiving and holding a sample of material, such as a bodily fluid (e.g., blood, urine, salvia) or solid (e.g., soil, spores, chemical residue) that is liquid soluble. The sample cartridge 110 can be a walled structure having one or more fluid channels and connection ports. The sample cartridge 110 may be relatively small, such that it can be easily be hand-held, portable, and/or disposable. An example of such a cartridge (useable with the system 100) is disclosed in U.S. Pat. No. 6,660,228, which is incorporated by reference herein.

The sample cartridge 110 can hold one or more reagents and/or chemicals that are used to process a sample, in order to ultimately detect some property of the sample. One example of such a process is PCR, which is used to amplify the presence of DNA. The sample cartridge 110 can include a sample chamber 110a, which is where the sample can be subjected to thermal cycling.

The sample cartridge 110 can interface with a thermal cycling module 120, such that the sample chamber 110a is thermally coupled thereto. The thermal cycling device 120 includes one or more apparatuses 120a configured to deliver energy to, and also remove energy from, the sample chamber 110a. Accordingly, at least one apparatus 120a, such as an electric heater, of the thermal cycling apparatus 120a can deliver heat to the sample chamber 110a, and at least one more apparatus 120b, can cool the sample chamber 110a to remove the heat. Such heating and cooling can be performed in a cyclic manner.

A sample preparation module 130 also interfaces with the sample cartridge 110. The sample preparation module 130 is configured to process the sample within the sample cartridge 110 before and/or after the sample is thermally cycled. The module 130 can include one or more devices to affect movement of the sample within the cartridge 110. For example, one device 130a can connect to a port of the cartridge in order to supply a negative or positive pressure, which can be used to move the sample to different portions of the cartridge 110, such as the sample chamber 110a. Such a device could be a vacuum pump or a plunger, or an electric motor used to power a sample movement mechanism within the sample cartridge 110. Another device 130b of the module 130 may apply energy to the sample, e.g., ultrasonic vibration, in order to physically disrupt the sample into a simpler form and/or affect a chemical reaction with one or more reagents and/or chemicals. Such a device could incite vibration via a piezoelectric device.

A sensor module 140 also interfaces with the sample cartridge 110. The sensor module 140 may include one or more sensors 140a and circuits 140b configured to generate signals based on detectable properties of the sample. These signals can be processed to ultimately provide useful data. For example, the sensor module 140 may include a detector and an energy source for providing electromagnetic energy to the sample in order to cause a reaction, detect an absorbance of the energy, or detect an excitation caused by the energy. A sensor 140a can be optically based, and include one or more cameras, such as a CCD.

The thermal cycling device 120, sample preparation module 130, and sensor module 140 can be physically and/or electrically integrated with one another, wholly or in-part. For example, these aspects can be housed within a greater testing module 150, which is configured specifically for one or more processes. The testing module 150 can be physically implemented within a multi-walled structure, such as a portable modular housing, and further include a controller 160. The controller 160 is configured to provide the thermal cycling device 120, sample preparation module 130, and/or sensor module 140, with control commands based on electrical inputs received from the modules.

The testing module 150 can interface with a computing module 170. In some embodiments, the testing module 150 receives power and commands exclusively from the computing module 170. Conversely, in other embodiments, the testing module may be self-powered (e.g., via an internal battery) and/or locally powered (e.g., via a wall outlet connection), and have a memory device configured to store testing results from the sensor module 140 for later delivery to the computing module 170. In such embodiments, the power and memory aspects can be incorporated as sub-aspects of the sensor module 140. Yet, in further embodiments, the testing module can be independently powered (e.g., battery, wall plug) but reliant on the computing module 170 to receive control commands via a direct (e.g., wired) or indirect (e.g., wireless) connection.

The computing module 170 can be a general purpose computer, special purpose computer, server, or cluster of servers. Generally, the computing module 170 includes at least one processor, connected by a communications bus to various types of physical memory (e.g., RAM, processor cache, HDD) and input/output devices (e.g., keyboard, monitor). Methods for operating the testing module 150 can be stored, permanently or as operationally needed, as machine readable instructions in the various types of memory. Accordingly, the processor can execute the instructions to perform the methods.

II. Thermal Cycling Module:

FIGS. 2A-2G shows a thermal cycling device 200, which is an embodiment of thermal cycling device 120.

The thermal cycling device (TCD) 200 is a modular component for cyclically providing heat and cooling to a testing sample. The TCD 200 includes a chamber 202 partially defined by a mounting wall 204, which also serves as a support for component mounting. The mounting wall 204 can be integrated with a greater enclosure, such as the testing module 150. The mounting wall 204 can be constructed of one or more layers of rigid material, such as aluminum, steel, or plastic. The mounting wall 204 can include a first mounting surface 206, that can be readily accessed for insertion of a sample cartridge. The second mounting surface 208 can be a portion of a structural member, such as a portion of sheet metal or molded plastic. The mounting wall 204 can also include a second mounting surface 208, which is generally inwardly facing and not readily accessible by a user. The second mounting surface 208 can be a portion of a PCB board having traces for supplying electric signals to devices mounted thereto.

Extending transversely from the second mounting surface 208 is a sample interfacing wall 210. The sample interfacing wall 210 can be a PCB board in electrical communication with the mounting wall 204. The sample interfacing wall 210 provides a support structure for a planer interface 212. The planar interface 212 is a specialized female connector that extends into the sample interfacing wall 210. The planar interface 212 includes two planar heating elements 214 opposing one another, with an open space therebetween configured to receive a male connector.

The planar interface 212 also includes sensors which are configured to detect aspects of the sample through edges of the male connector. This arrangement is well shown in FIG. 2G. The male connector includes a planar sample chamber (e.g., of sample cartridge 110) that is inserted into the planar interface 212. The planar heating elements 214 each provide a relatively large surface area (e.g., 170 mm$^2$ each) to transfer heat to corresponding planar sides of the planar sample chamber, each of which can have a comparatively smaller surface area (e.g., 16 mm$^2$ each).

A plurality of air sources can be coupled, directly or indirectly, to the second mounting surface 208 and/or the sample interfacing wall 210. In some embodiments, the plurality of air sources includes a first air source 216a, second air source 216b, third air source 216c, and a fourth air source 216d.

As shown, the first air source 216a is positioned on one side of the sample interfacing wall 210, such that a planar face 218a of the first air source 216a is arranged to be substantially parallel with the sample interfacing wall 210. In some embodiments, the first air source 216a and sample interfacing wall 210 are separated by a distance of approximately 9.5 mm. The second air source 216b is positioned such that a planar face 218b, or a virtual planar extension thereof, of the second air source 216b intersects with the sample interfacing wall 210 such that an acute angle is present therebetween, which here is shown to be approximately 45°. A third air source 216c and a fourth air source 216d are likewise positioned on the other side of the sample interfacing wall 210.

The arrangement of the air sources 216 is shown to be substantially symmetrical about the sample interfacing wall 210. However, symmetry is not required, and thus an asymmetric arrangement is also possible. Further, in some embodiments the third air source 216c and a fourth air source 216d are not present. In other embodiments, only the first air source 216a and fourth air source 216d are present.

The second air source 216b and the third air source 216c can be connected to the sample interfacing wall 210 by elongated supports 220a, which are affixed to the sample interfacing wall 210. The elongated supports 220a can each include a trough configured to hold an edge of an air source 216. Likewise, the first and fourth air sources 216a/216d can be connected to the second mounting surface 208 via elongated supports 220b, which can each include a trough configured to hold an edge of an air source. Accordingly, as shown each air source 216 is directly or indirectly "edge mounted" to the sample interfacing wall 210 and second mounting surface 208, such that the planar face of each air source 216 is substantially transverse to the second mounting surface 208.

Figure 2A:
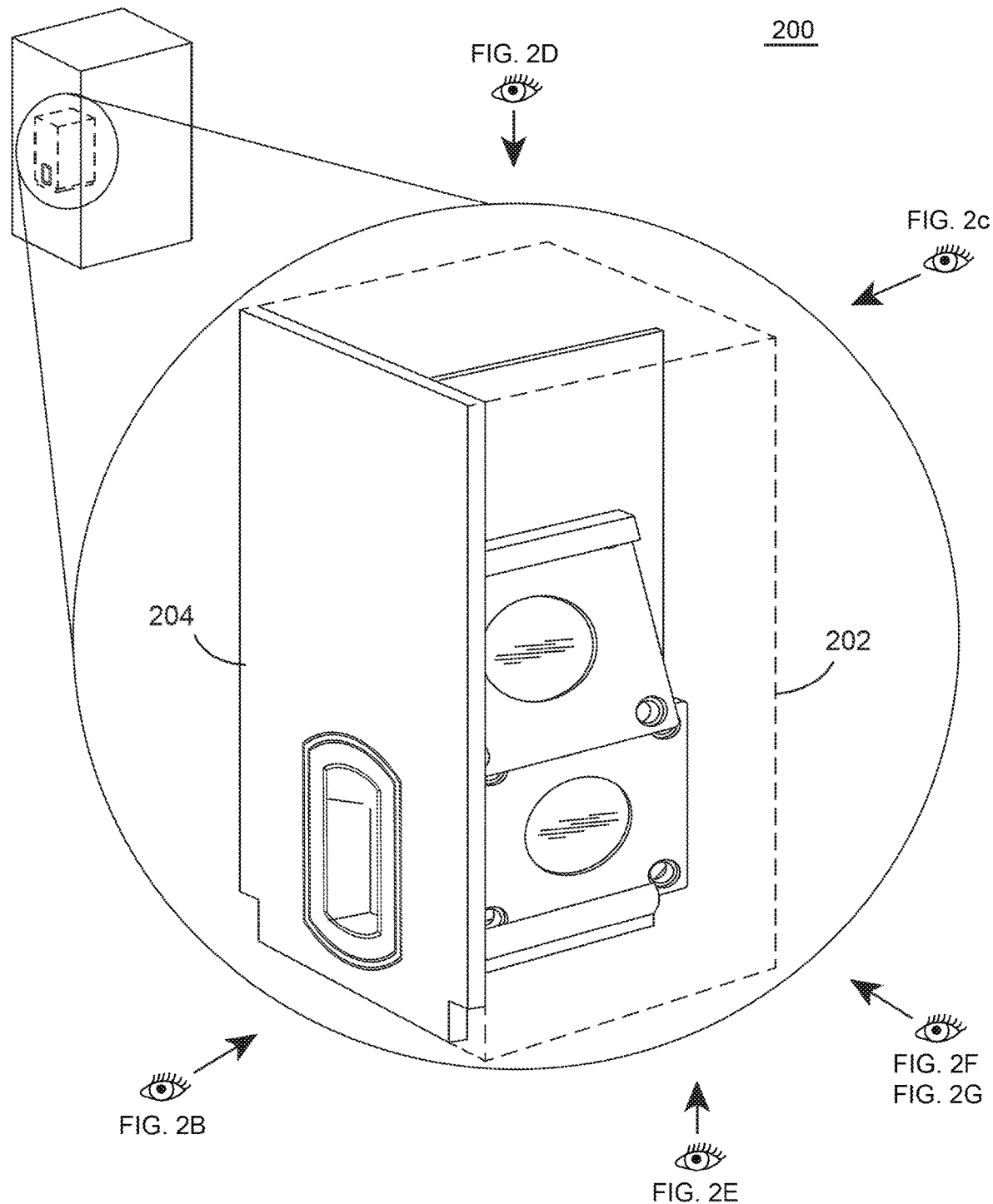
FIG. 2A is a perspective view of a thermal cycling device, according to some embodiments of the invention.
Figure 2B:
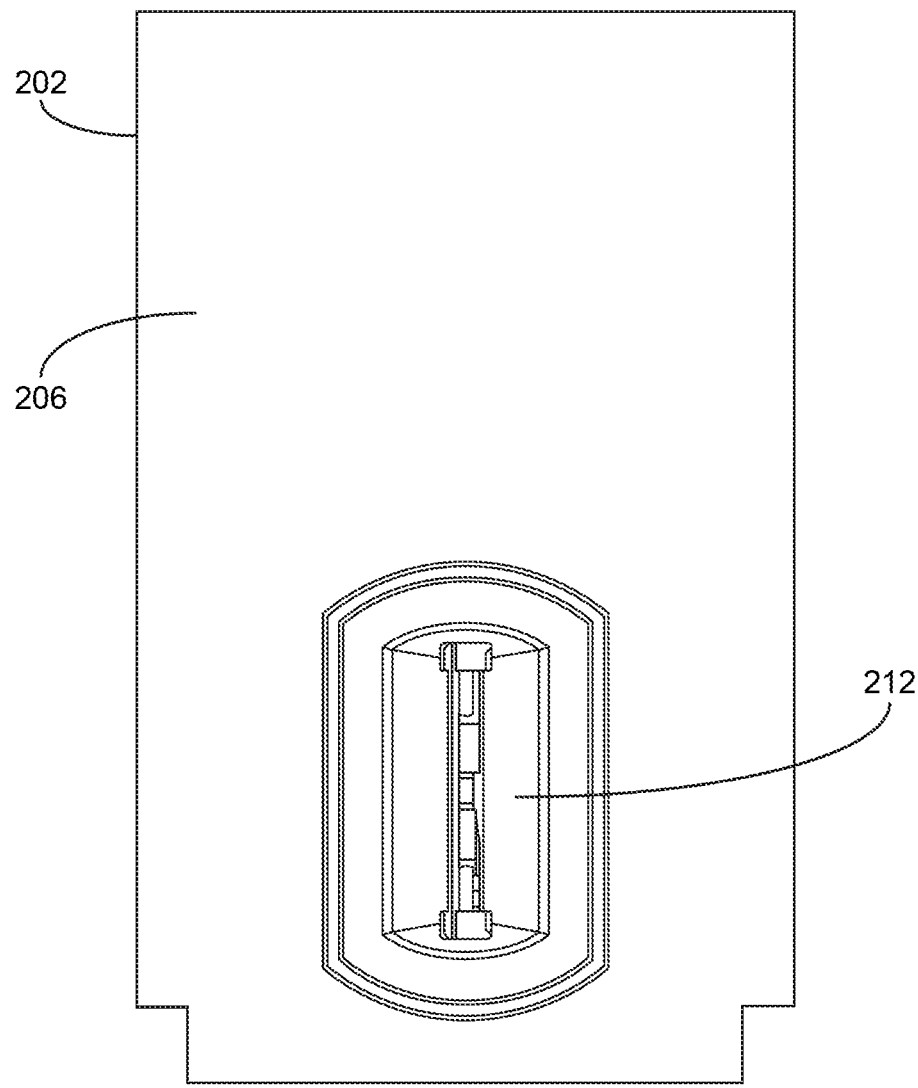
FIG. 2B is a front view of the thermal cycling device of FIG. 2A.

Extents of the sample interfacing wall 210 and the second mounting surface 208 partially define a chamber of the system 100, as shown by the dashed lines in FIG. 2A. Put another way, the chamber is a volume that is at least determined by area of the second mounting surface 208 multiplied by the extension length of the sample interfacing wall 210 from the second mounting surface 208. The first air source 216a, second air source 216b, second mounting surface 208, and sample interfacing wall 210 partially define a first sub-volume V1 within the chamber. Likewise the third air source 216c, fourth air source 216d, second mounting surface 208, and sample interfacing wall 210 partially define a second sub-volume V2 within the chamber.

The first air source 216a and fourth air source 216d are arranged such that corresponding exit ports 222a/222d on planar faces 218a/218d directly point at planar heating elements 214 on the planar interface 212. Air inlets 224 are also generally provided on each air source 216 opposite to the exit ports 222. Accordingly, air streams exiting the exit ports 222a/222d are vectored to intersect the planar heating elements 214 of the planar interface 212, to affect a sample chamber of a connected cartridge. The second air source 216b and third air source 216c are arranged such that corresponding exit ports 222b/222c directly point at positions on the sample interfacing wall adjacent to or at the same location ports 222a/222d are directed to. Accordingly, air streams exiting the exit ports 222b/222c are vectored to intersect the sample interfacing wall at an acute angle, i.e., less than 90°. As shown, the angle of intersection for exit ports 222b/222c is approximately 45°.

In use, the TCD 200 can rapidly thermally cycle a sample held by the planar interface 212 between relatively low and high temperatures. The sample will be brought from a high or low temperature to a low or high temperature, which is performed by one or more controllers operating the planar heating elements 214 and cooling performed by the air sources 216. Thermal cycling is required for some biological testing processes, such as PCR. For PCR, a sample will typically be held at a low temperature of 60° C. for a predetermined amount of time and ramped up to a high temperature of 94° C. for another predetermined amount of time. Ramp times, both up and down, between periods of low and high temperatures are desired to be relatively short compared to sustained periods of low and high temperatures. Accordingly, a plot of temperature over time would ideally resemble a square wave.

Before the thermal cycling process begins, the planar heating elements 214 can be powered ON to preheat the sample from an as-delivered temperature (e.g., room temperature) to a baseline low temperature (e.g., 60° C.) for a predetermined amount of time (e.g., 6 sec) and subsequently ramped up to a high temperature (e.g., 94° C.) for a predetermined amount of time (e.g., 6 sec), or alternatively, directly from the as-delivered temperature to the high temperature for a predetermined amount of time.

After the high temperature period is complete, the planar heating elements 214 are turned OFF, or provided with less power, and the air sources 216 are turned ON to cool the sample and bring the temperature back to the low temperature for a predetermined amount of time (e.g., 6 sec). Once the low temperature period has ended, the air sources 216 are powered OFF and planar heating elements 214 can once again be powered ON such that the sample is ramped back up to the high temperature for a predetermined amount of time. This cycling process continues until a predetermined amount of cycles have been completed. Generally the duty cycles for the planar heating elements 214 and air sources 216 can be substantially (with minor overlap) out of phase with each other, such that the devices are not operating at the same time. However, during the low and high temperature periods, power to the planar heating elements 214 and/or the air sources 216 can be provided as needed (i.e., intermittently at full/partial power or continuously at partial power), to maintain the sample at the required low or high temperature.

Figure 2C:
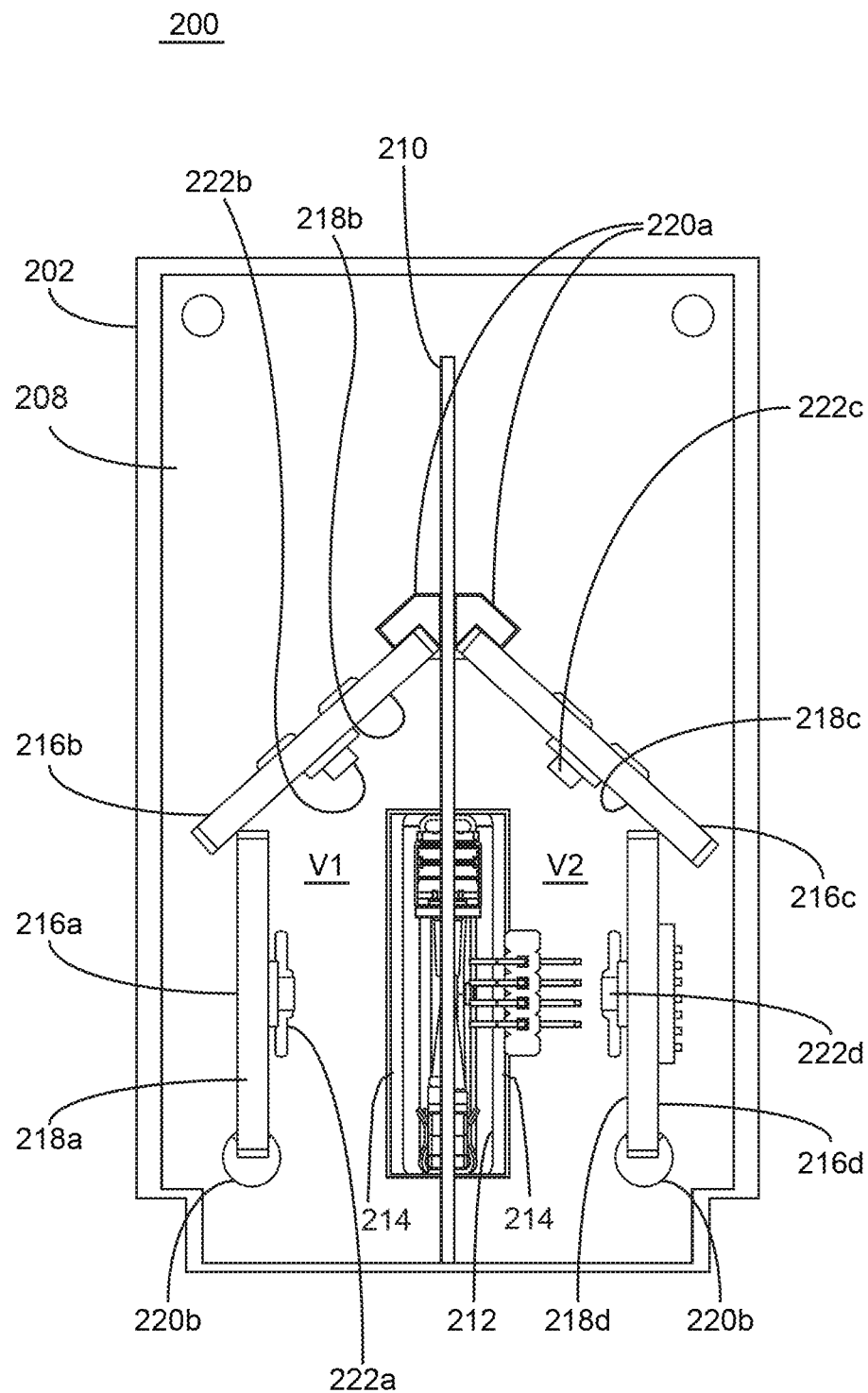
FIG. 2C is a rear view of the thermal cycling device of FIG. 2A.
Figure 2D:
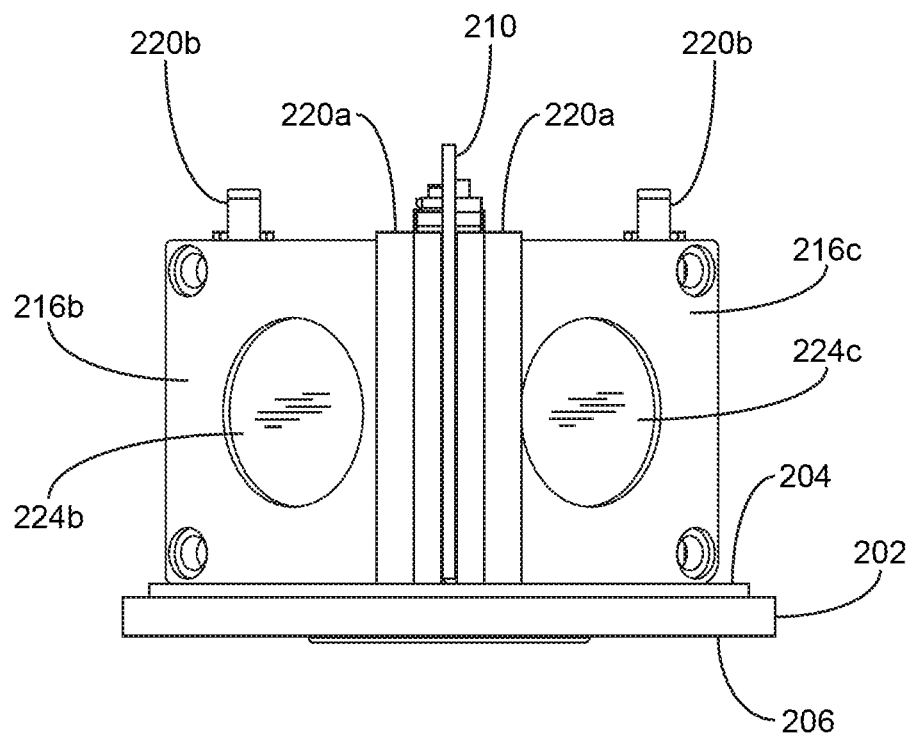
FIG. 2D is a top view (downward facing) of the thermal cycling device of FIG. 2A.
Figure 2E:
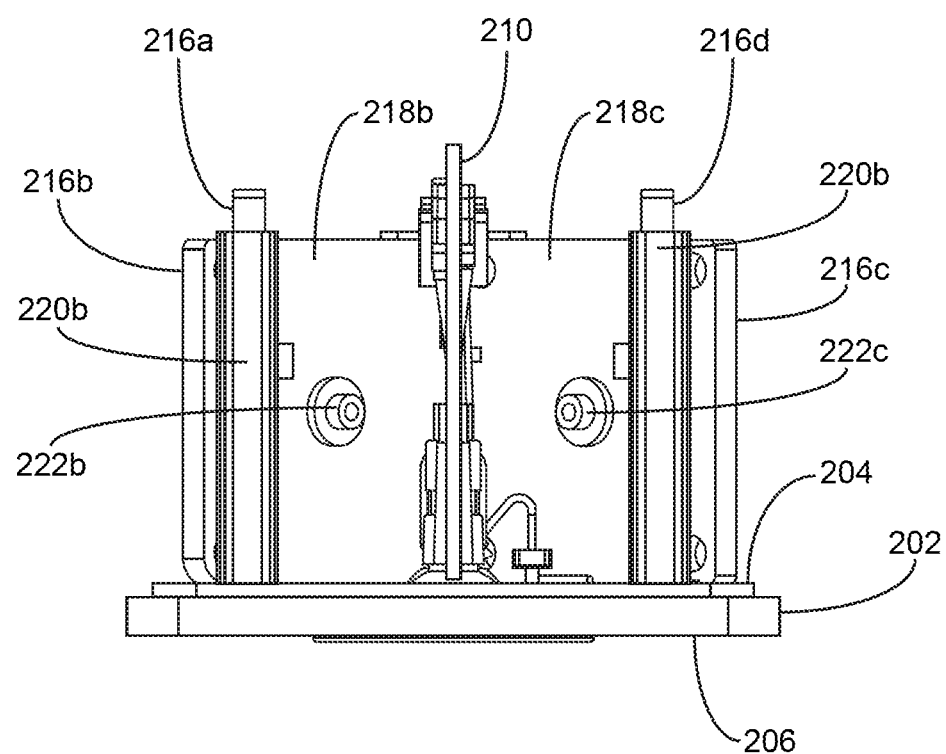
FIG. 2E is a bottom view (upward facing) of the thermal cycling device of FIG. 2A.
Figure 2F:
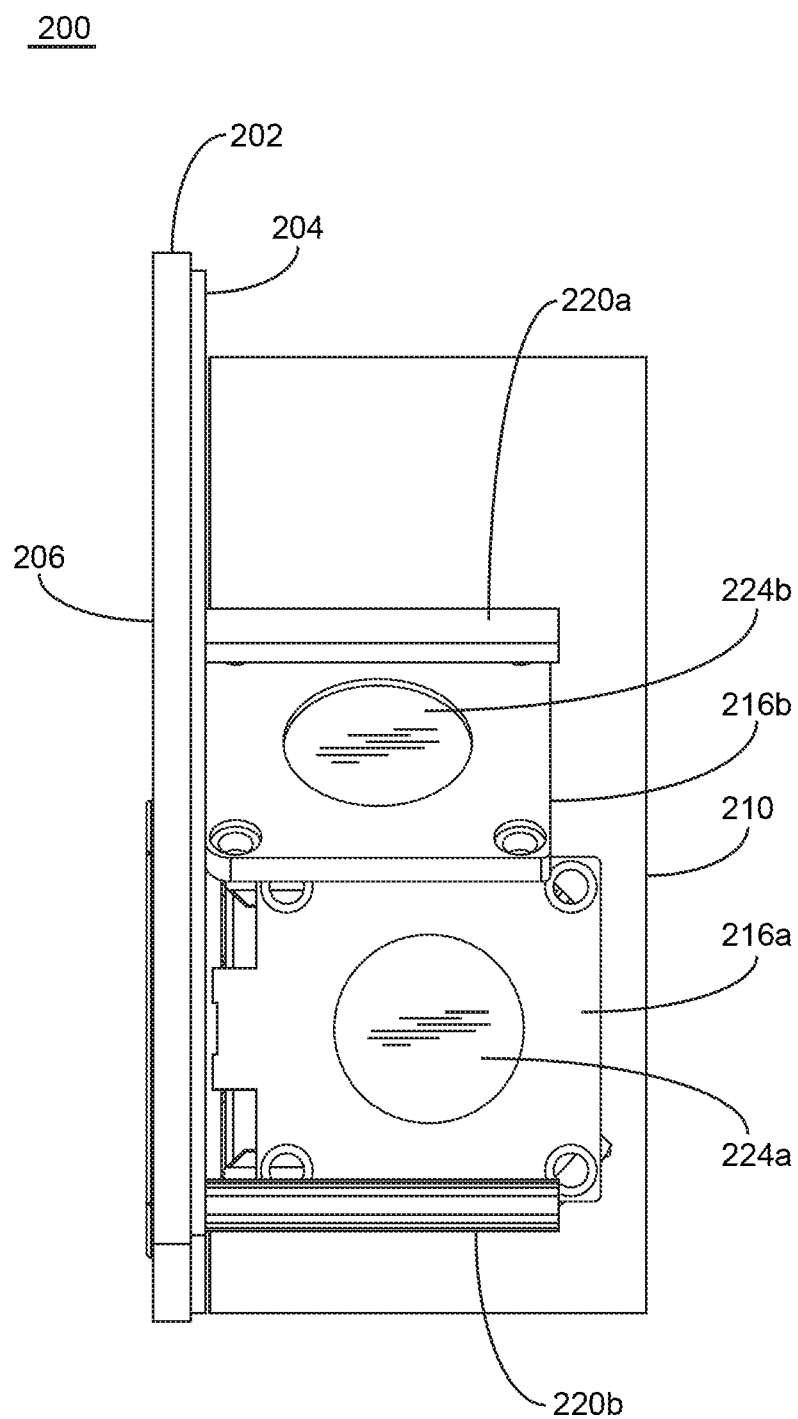
FIG. 2F is a side view of the thermal cycling device of FIG. 2A.
Figure 2G:
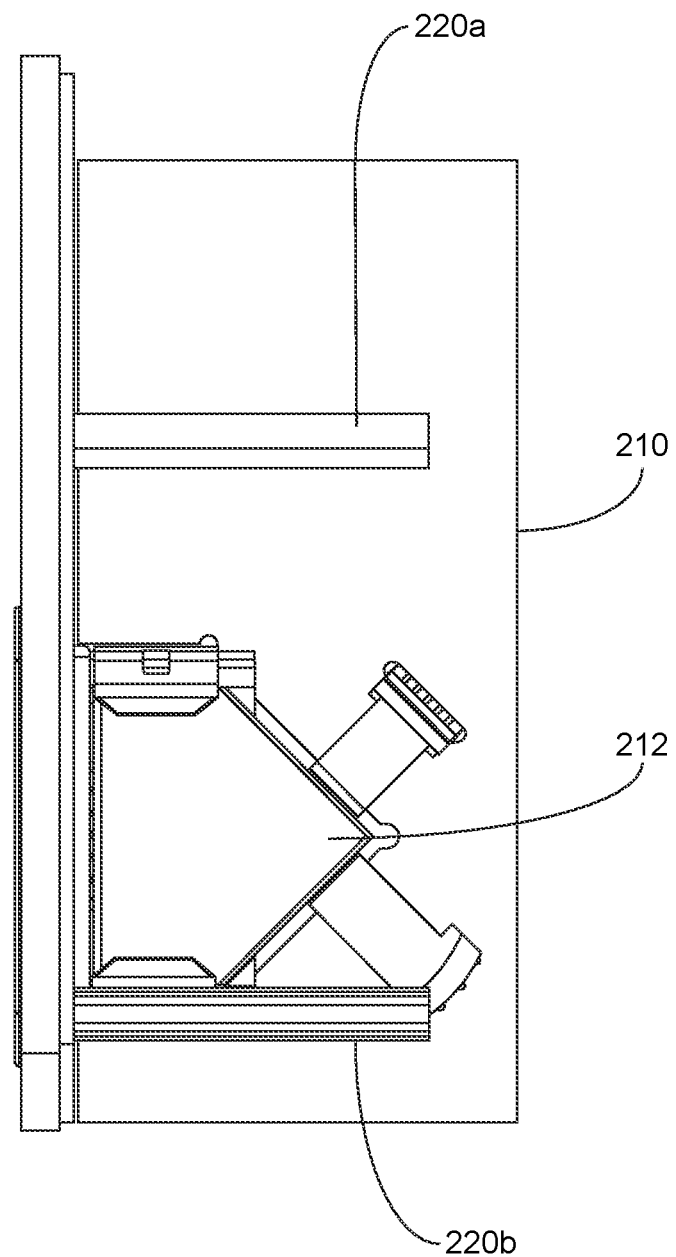
FIG. 2G is the side view of FIG. 2F with components removed for clarity.
Figure 2H:
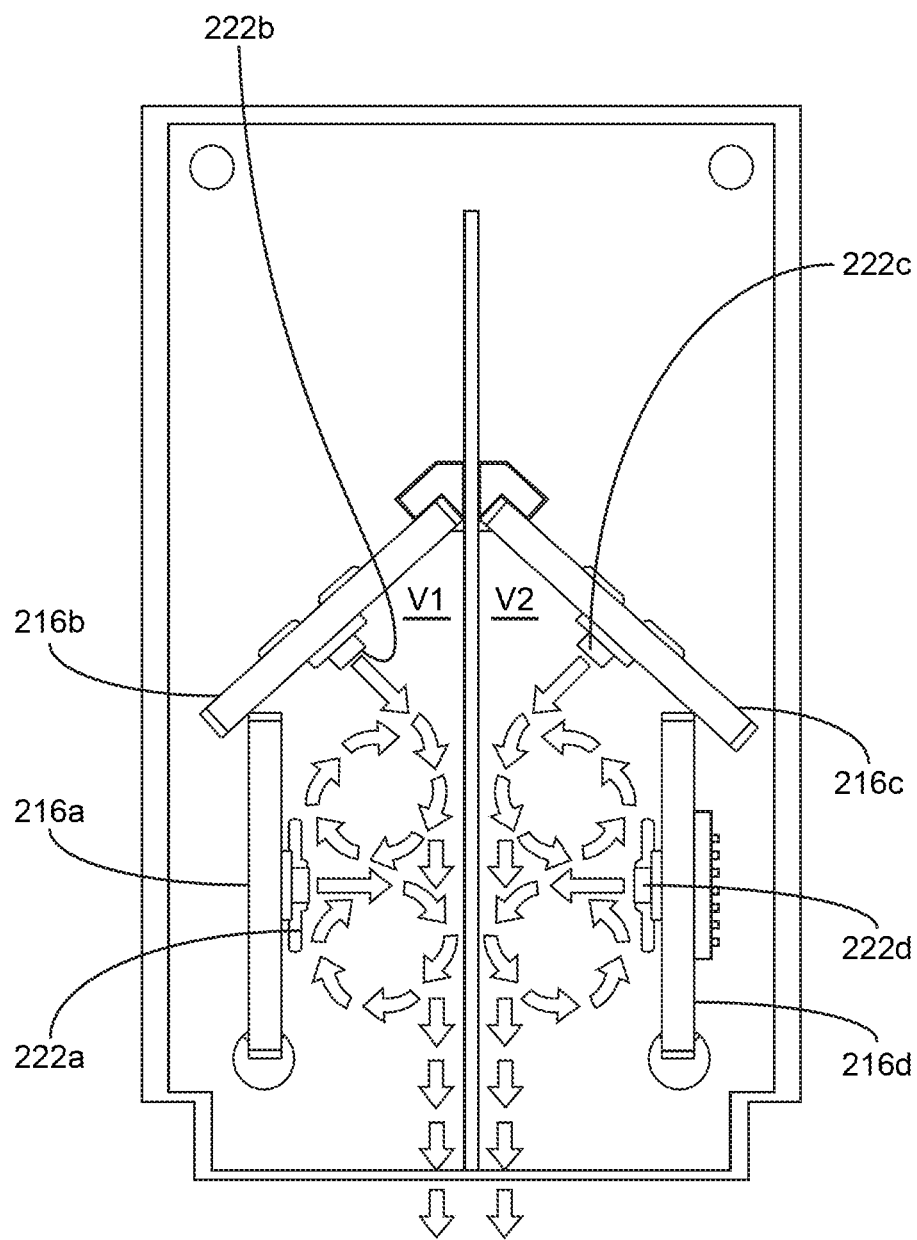
FIG. 2H is a simplified rear view of the thermal cycling device of FIG. 2A in use, according to some embodiment of the invention.

Fluid flow dynamics occurring during the cooling period are simplistically depicted in FIG. 2H. As shown, the respective planar faces 218a/218d of air sources 216a/216d are arranged parallel to the sample interfacing wall 210 and planar interface 212 (not shown in this view for clarity), and are emitting air streams from exit ports 222a/222d that transversely intersect the planar interface 212. Such an arrangement is very effective because it creates turbulent airflow about the planar heating elements 214, which in-turn provides effective cooling within sub-volumes V1/V2 between the sample interfacing wall 210 and the air sources 216a/216d.

Thus, it should be understood that the air sources 216a/216d are not merely sources of forced convection, but also structural members that provide a confined environment for efficient forced convection heat transfer, thus reducing the overall footprint of the TCD 200 and also lowering volumetric flow requirements for the air sources 216a/216d. Put another way, the farther the air sources 216a/216d are from the planar heating elements 214, the more powerful the air sources 216a/216d need to be to meet a stated cooling requirement, because air velocity dissipates with increasing distance—the air source arrangement addresses this by placing forced convection sources relatively close (e.g., 9.5 mm) to the planar heating elements 214, thus, the air sources 216a/216d can have relatively low volumetric flow capability in relation to the heat generated by the planar interface 212, allowing for a compact design. Further, the larger the volume that the planar heating elements 214 reside in, the more powerful the air sources 216a/216d need to be to meet the stated cooling requirement, since the larger volume provides less structure for formation of circulatory eddy currents—the disclosed air source arrangement addresses this by providing the air sources with surrounding planar faces for turbulent air to circulate.

The air within the sub-volumes V1/V2, however, can quickly become heated, and thus cooling efficiency may decrease over one or several thermal cycles. To help counter this, air sources 216b/216c are arranged to direct the heated air out of the sub-volumes V1/V2 and help replenish the sub-volumes V1/V2 with unheated air.

As shown, the respective planar faces 218b/218c of air sources 216b/216c are angularly arranged with respect to the sample interfacing wall 210, such that planar faces 218b/218c, or virtual extensions thereof, intersect with the sample interfacing wall 210 to form acute angles therebetween. As shown, the air sources 216b/216c are emitting air streams from exit ports 222b/222c that angularly intersect the planar interface 212. These air streams work to direct heated air out of sub-volumes V1/V2 by pushing the heated air out of exits of the sub-volumes V1/V2. Here, air is pushed out towards a bottom direction, along the sample interfacing wall 210, and also a rearward direction (transverse to the mounting wall 204). The air sources 216b/216c also further limit the confines of the sub-volumes V1/V2 and thus provide a discreet air flow paths into and out of the sub-volumes V1/V2.

The embodiment of the TCD 200 shown in FIGS. 2A-2H includes four air sources 216 having a symmetrical arrangement about the sample interfacing wall 210. This arrangement is very effective, however, it should be understood that other beneficial arrangements are also possible.

Figure 3A:
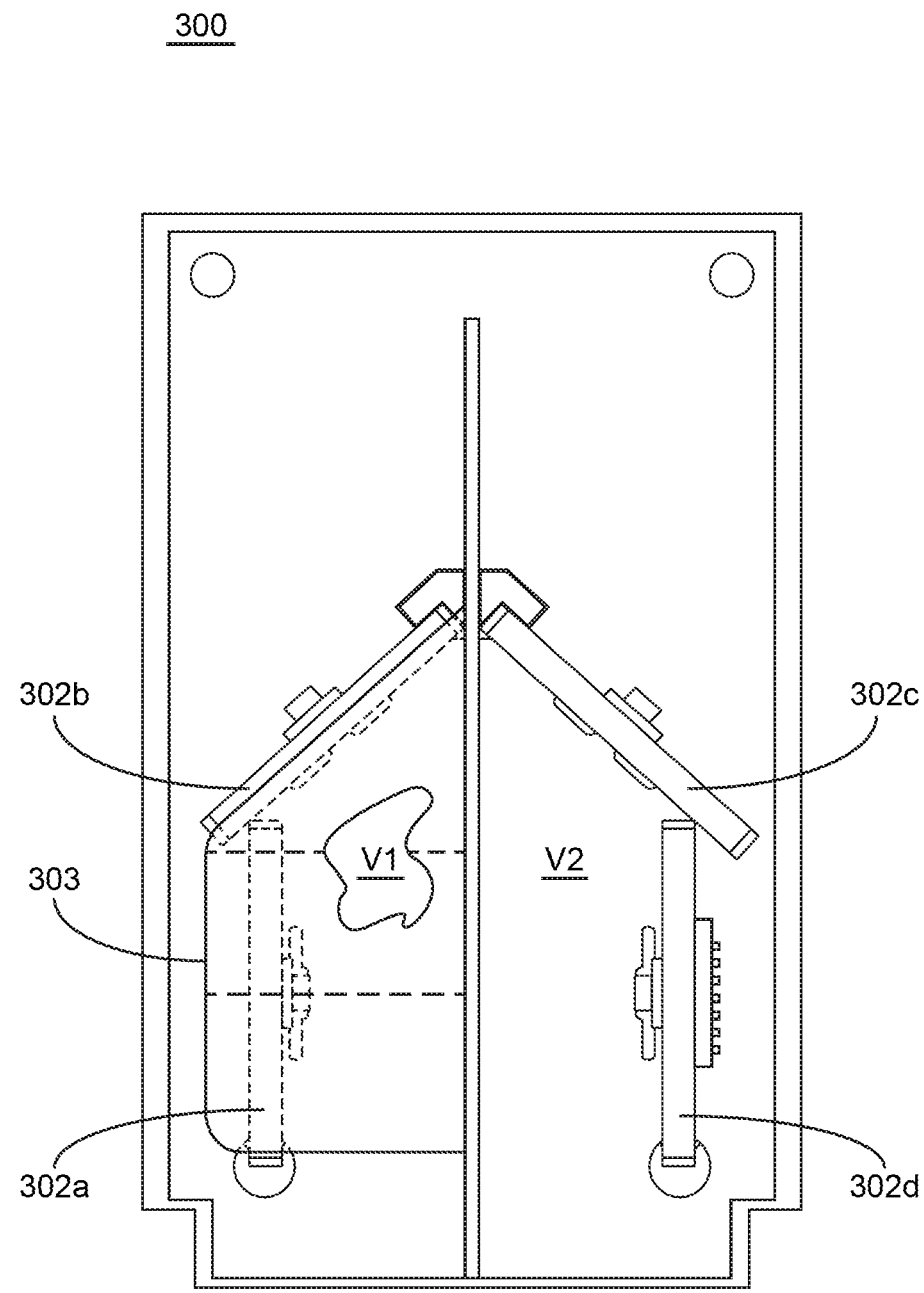
FIGS. 3A-3E are rear views of thermal cycling devices, according to respective embodiments of the invention.

III. Alternative TCD Arrangements:

FIG. 3A shows a TCD 300 having a similar arrangement to TCD 200, with four air sources 302a/302b/302c/302d arranged in an almost identical manner. Here, TCD 300 differs from TCD 200 in that air sources 302b and 302c are angularly arranged such that their exit ports face away from the interior sub-volumes. Accordingly, air inlets for air sources 302b and 302c are in direct communication with sub-volumes V1/V2. In use, air sources 302a/302d operate as described with reference to TCD 200, however, heated air created within sub-volumes V1/V2 will be diverted into and out off air sources 302b and 302c. Thus, air sources 302b/302c apply suction to the heated air within sub-volumes V1/V2, which is replaced with fresh air from the bottom and rearward directions. In some embodiments, optional top covers 303, covering all or a portion of the lateral openings, are used to such that air is primarily drawn into the sub-volumes V1/V2 from the bottom direction. The dashed lines show the variable configurations of the top cover. Only one cover 303 is shown for brevity, however, both sides may have a cover 303 over sub-volumes V1/V2.

Figure 3B:
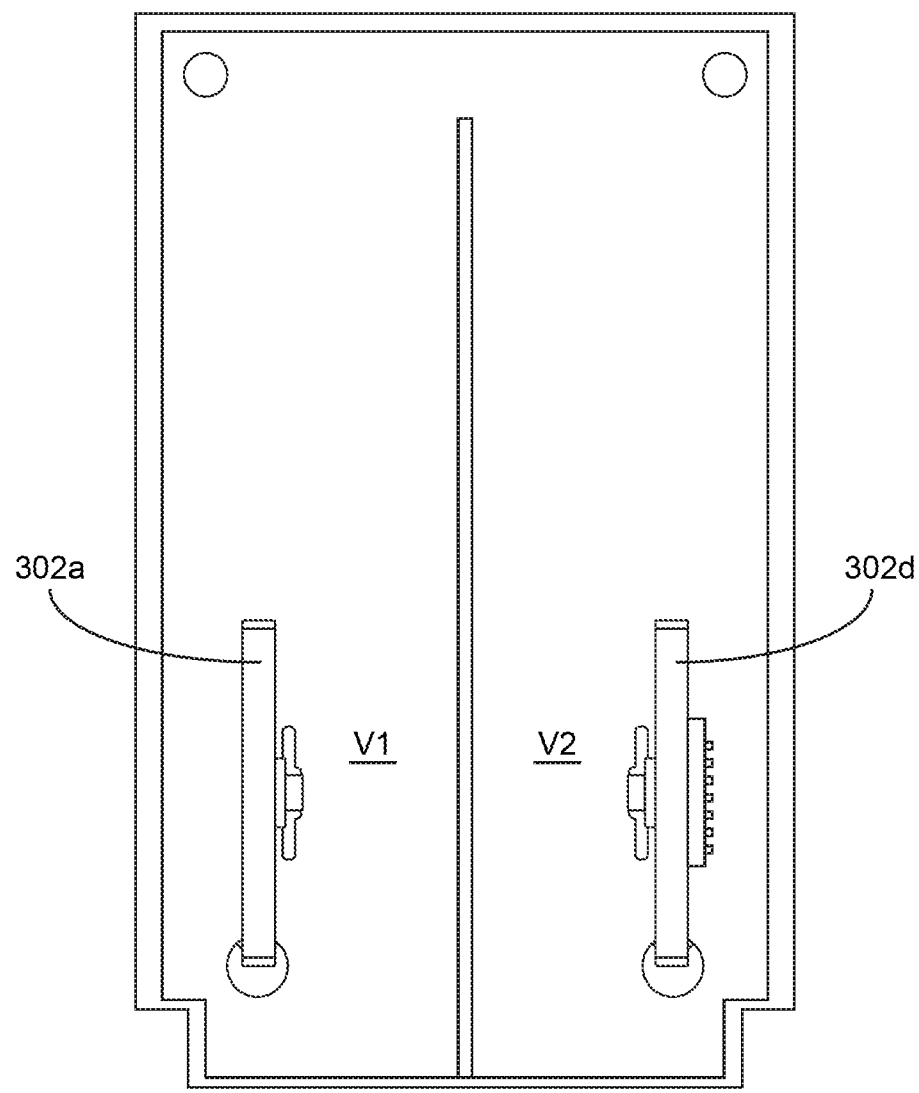

FIG. 3B shows a TCD 304 having a similar arrangement to TCD 200, however, here only two air parallel sources 302a /302d are provided. In some embodiments, this arrangement is sufficient to provide a required level of cooling performance, since natural convection will evacuate heated air in the upward direction, and power to the air sources 302a /302d may also be increased accordingly.

Figure 3C:
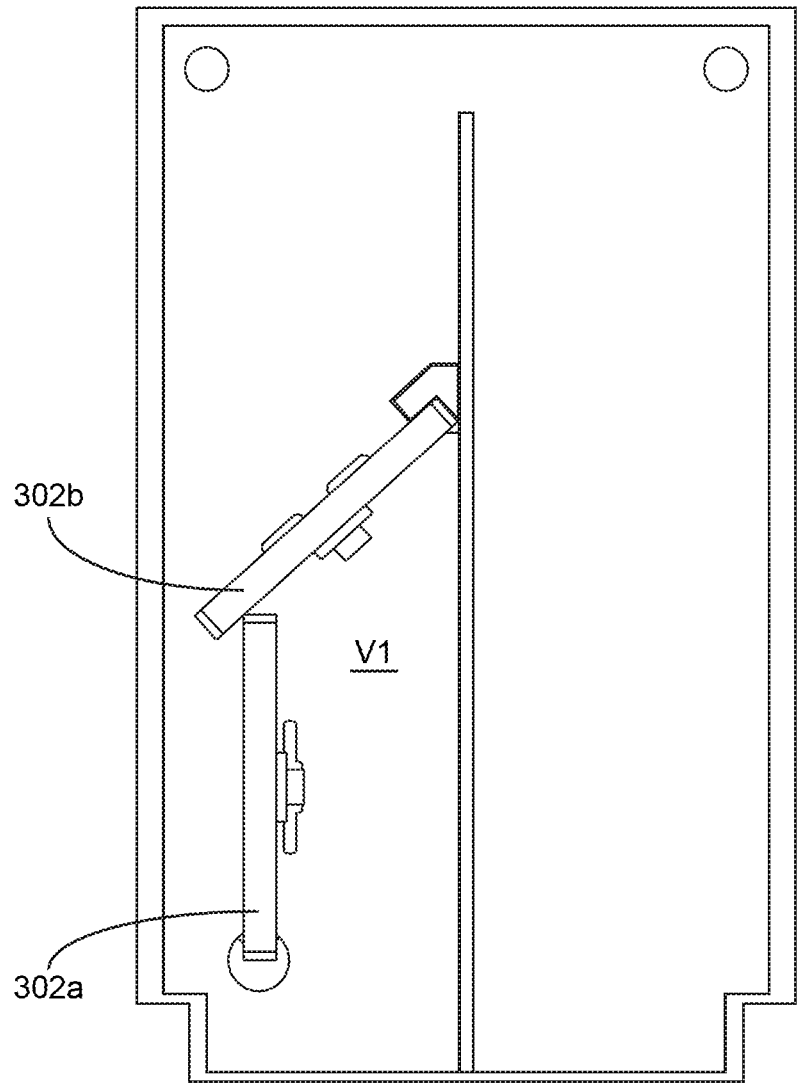

FIG. 3C shows a TCD 306 having a similar arrangement to TCD 200, however, here only two air sources 302a /302b are provided, which are asymmetrically arranged to only provide forced convection into sub-volume V1. In some embodiments, this arrangement is sufficient to provide a required level of cooling performance, and power to the air sources 302a /302b may also be increased as needed.

Figure 3D:
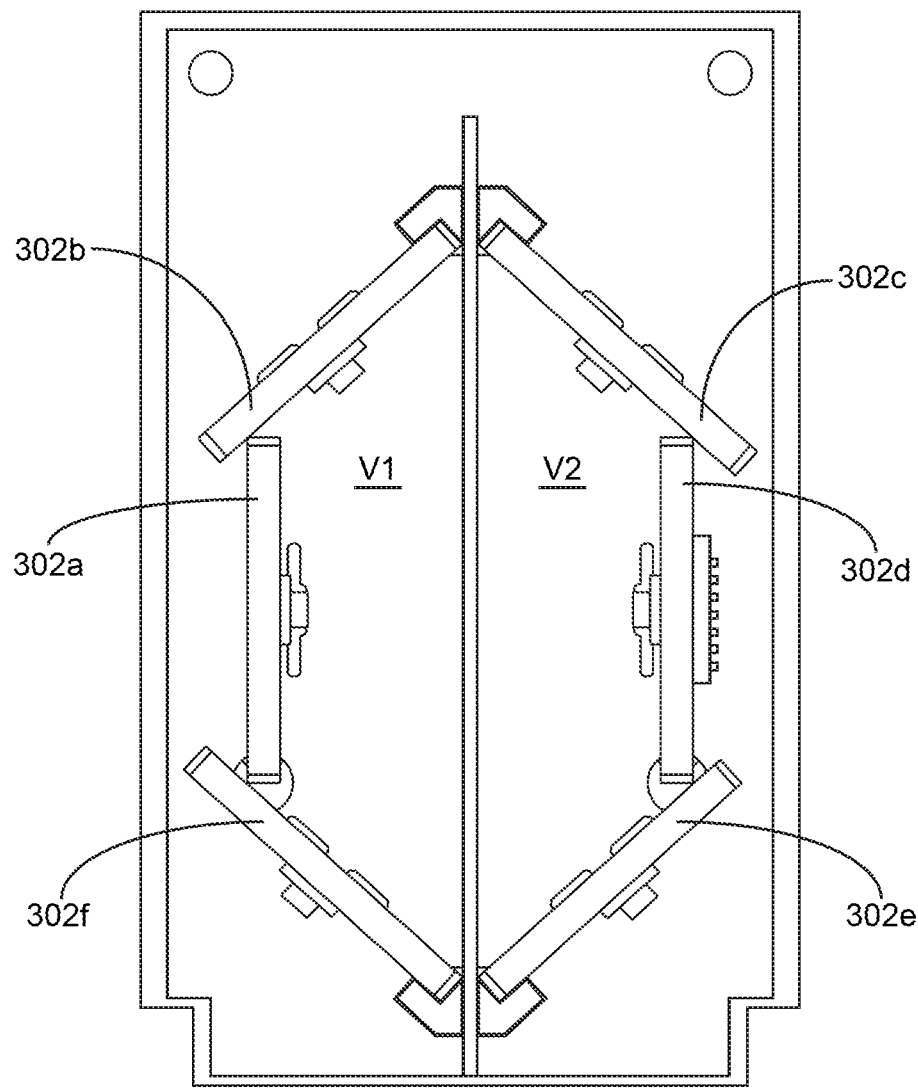

FIG. 3D shows a TCD 308 having a similar arrangement to TCD 200, however, here two additional air sources 302e /302f are provided, which are arranged to apply suction to heated air within sub-volumes V1/V2. In some embodiments, this arrangement is required to provide a sufficient level of cooling performance.

Figure 3E:
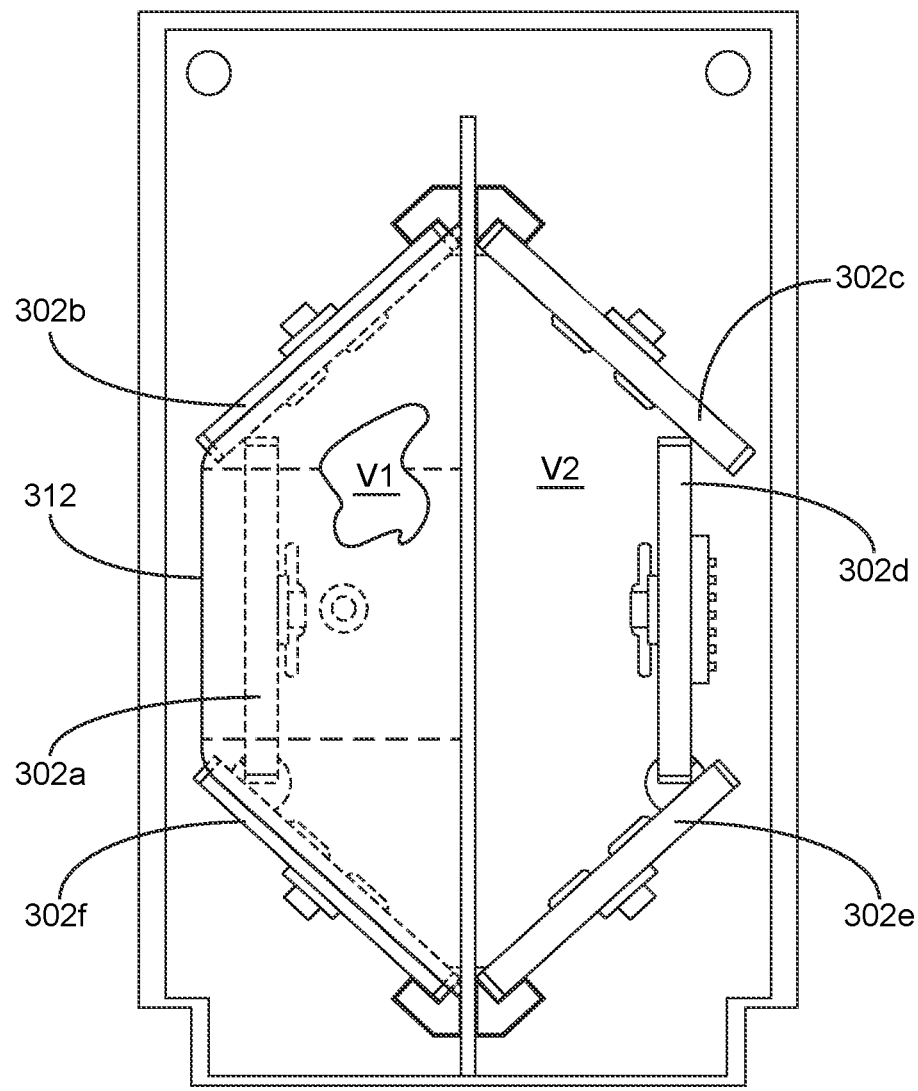

FIG. 3E shows a TCD 310 having a similar arrangement to TCD 308, however, here all angularly arranged air sources 302b /302c /302e /302f are arranged to apply suction sub-volumes V1/V2. In some embodiments, this arrangement is used to provide a sufficient level of cooling performance. In some embodiments, optional top covers 312, covering all or a portion of the lateral openings, are used to such that air is primarily drawn into air into the sub-volumes V1/V2 primarily from air sources 302a /302d. Further, in some embodiments, the cover may fluidically seal the sub-volumes V1/V2, such that air sources 302a /302d provide the only source of fresh air. In such embodiments, this may increase the performance of air sources 302a /302d by lowering back pressure, since air sources 302b /302c /302e /302f can be driven to suction air out at a higher rate than air sources 302a /302d can provide. Thus, the work load on the air sources 302a /302d is reduced, which can result in greater volumetric output for a given power input to the air sources 302a /302d. The dashed lines show the variable configurations of the top cover. Only one cover 312 is shown for brevity, however, both sides may have a cover 312 over sub-volumes V1/V2. In some embodiments, top covers 312 may include an additional air source (shown by the dashed circles) arranged to either provide suction to or drive air into the sub-volumes V1/V2.

Figure 4A:
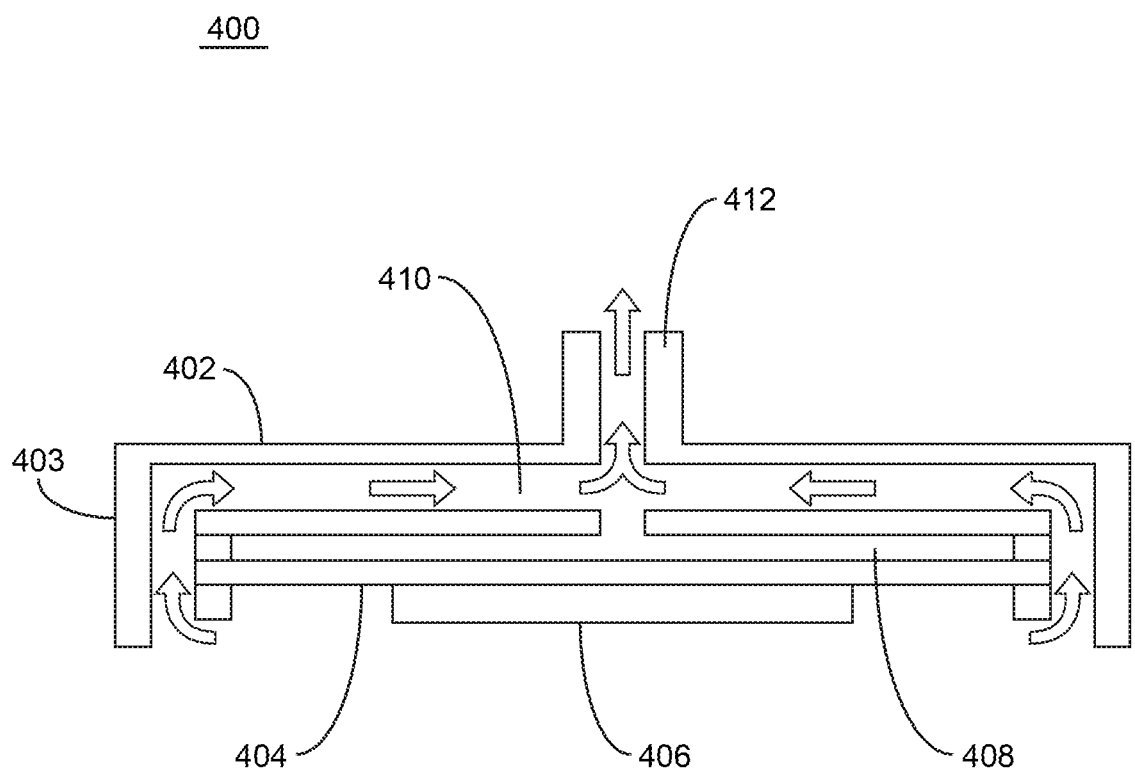
FIG. 4A is a cross-sectional view of an air source, according to some embodiments of the invention.

IV. Exemplary Cooling Source:

FIG. 4A shows an example of a cooling source 400 in cross-section. The cooling source 400 shares the substantially planar construction of the air sources (e.g., 202a) disclosed herein. The cooling source 400 is an air pump that includes a housing having a planar face 402 surrounded by four edges or sides 403. In some embodiments, the planar face 402 has dimensions of 20 mm×20 mm and each edge 403 has dimensions of 1.85 mm×20 mm. A piezoelectric device 406 is coupled to an internal diaphragm 404. The diaphragm 404 partially forms an internal pumping chamber 408. In use the piezoelectric device 406 is driven to vibrate diaphragm 404. This causes air to be drawn into the pump and evacuated out of nozzle 412, shown as airflow 410. The commercially available cooling source is the Microblower manufactured by Murata Mfg. Co., Ltd., which is rated, at a drive frequency of 26 KHz, to move 1 L/min at 15 Vpp under 100 Pa of back pressure. In some embodiments the cooling source 400 can be configured as a high velocity air pump, which in use operates with an internal static pressure less than 5 psi. In some embodiments the cooling source 400 can be configured as a high pressure air pump, which in use operates with an internal static pressure greater than 5 psi. The static pressure within the internal pumping chamber can be tuned by altering flow resistance where air is drawn in by the diaphragm 404 and/or where air exits at the nozzle 412 and/or at other positions within the cooling source 400.

Figure 4B:
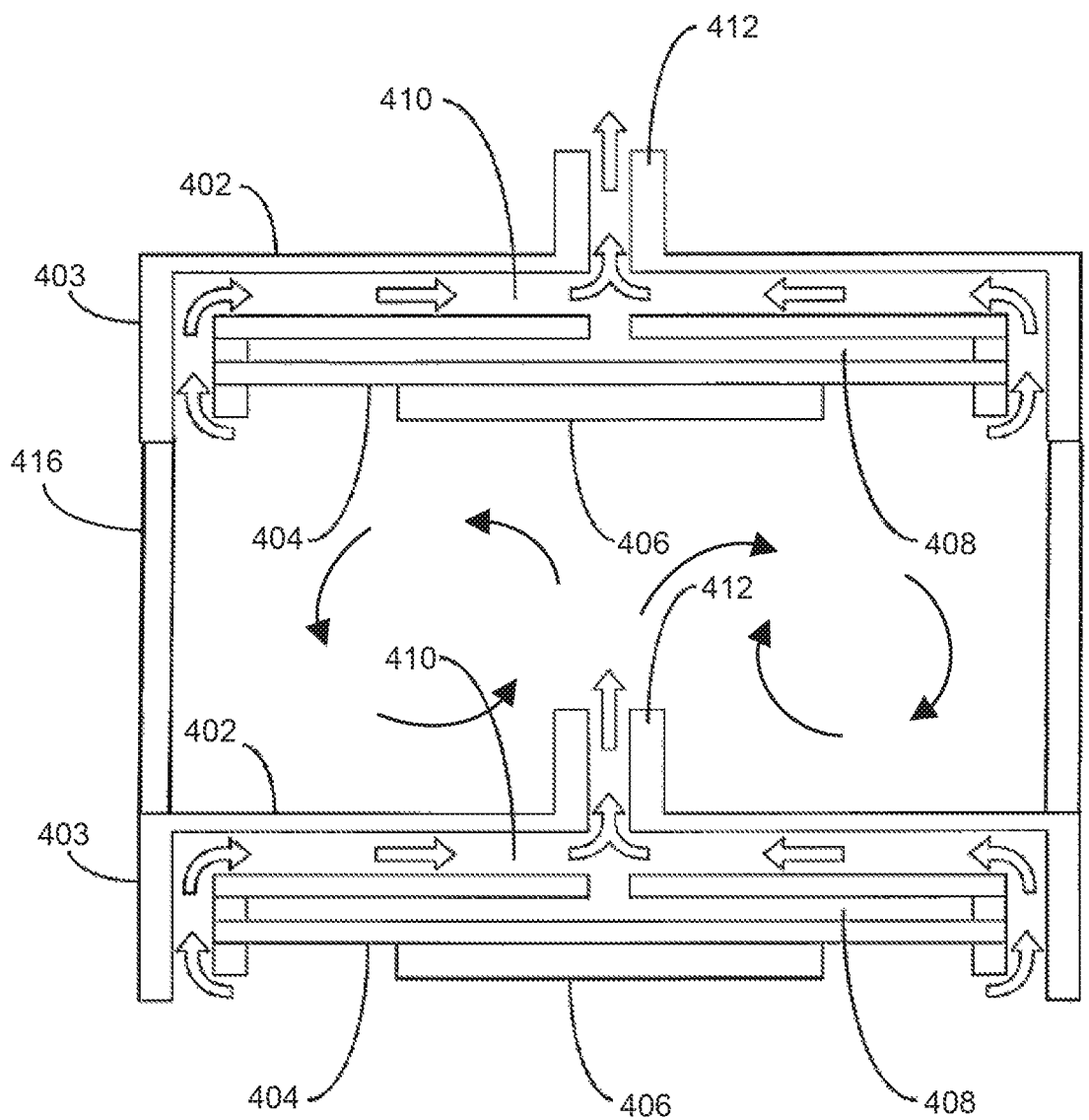
FIG. 4B is a cross-sectional view of a plurality of linked pressurized air sources, according to some embodiments of the invention.

FIG. 4B shows an example of a plurality of linked air sources 414 in cross-section. Here, the cooling source is includes at least two cooling sources 400, but may include more. A reservoir 416 is provided between the cooling sources 400 which is fluidly sealed therebetween. In this configuration, the cooling sources 400 are configured as high pressure air pumps. The cooling sources 400 and reservoir 416 are arranged such that air resistance from the bottom-most to top-most cooling source allows airflow 410 to flow therebetween.

In testing, cooling sources 400 were arranged as shown in FIG. 3B and were driven at 24 Vpp, which resulted in a volumetric output rate of approximately 1.4 L/min (0.05 CFM) for each cooling source ((total 2.8 L/min (0.1 CFM)), assuming a back pressure of approximately 100 Pa. This arrangement was found to slightly better the performance of a centrifugal fan (NIDEC GAMMA26 model A333-999) operating at 113 L/min (4 CFM) blowing air from the upward direction (with reference to the directions in FIG. 2A) from a distance of approximately 30 mm. The cooling sources 400 caused a heat source to drop from 95° C. to 60° C. in 7.5 sec, compared to the fan which took 7.6 sec. Accordingly, the inventive arrangement can at least equal the performance of the centrifugal fan, while only requiring approximately 2.5% of the centrifugal fan's volumetric output.

In another test, cooling sources 400 were arranged as shown in FIG. 2C. The cooling sources were driven at 16 Vpp, which resulted in a volumetric output rate of approximately 1.0 L/min (0.035 CFM) for each cooling source ((total 4 L/min (0.141 CFM)), assuming a back pressure of approximately 100 Pa. This arrangement caused a heat source to drop from 95° C. to 60° C. in 7.4 sec. Accordingly, this arrangement of cooling sources 400 can at least equal the performance of a centrifugal fan, while only requiring approximately 3.5% of the centrifugal fan's volumetric output.

In another test, cooling sources 400 were again arranged as shown in FIG. 2C. The cooling sources were driven at 20 Vpp, which resulted in a volumetric output rate of approximately 1.2 L/min (0.042 CFM) for each cooling source ((total 4.8 L/min (0.17 CFM)), assuming a back pressure of approximately 100 Pa. This arrangement caused a heat source to drop from 95° C. to 60° C. in 6.4 sec, which is a 16% improvement over the centrifugal fan. Accordingly, this arrangement of cooling sources 400 can significantly better the performance of a centrifugal fan, while only requiring approximately 4.3% of the centrifugal fan's volumetric output.

In yet another test, cooling sources 400 were again arranged as shown in FIG. 2C. The cooling sources were driven at 24 Vpp, which resulted in a volumetric output rate of approximately 1.4 L/min (0.05 CFM) for each cooling source ((total 5.6 L/min (0.2 CFM)), assuming a back pressure of approximately 100 Pa. This arrangement caused a heat source to drop from 95° C. to 60° C. in 5.8 sec, which is a 26% performance improvement versus the centrifugal fan. Accordingly, this arrangement of cooling sources 400 can significantly better the performance of a centrifugal fan, while only requiring approximately 5% of the centrifugal fan's volumetric output.

From these tests, it is evident that embodiments of the invention can equal or better the performance of a centrifugal fan. The centrifugal fan requires a relatively large operating environment given its physical size (approximately 50 mm×50 mm×15 mm), while embodiments of the invention add virtually no space requirements to a test system. Thus, size, power, and cooling efficiencies can be optimized using embodiments of the TCD. Further, the TCD provides much better response times, since excitation of the piezoelectric devices are near instantaneous.

FIGS. 5A-5E show schematically diagrams different diagrams of arrangements of pluralities of linked pressurized air sources ("stacks"), according to some embodiments of the invention. In some embodiments, a stack can be configured to provide impingement cooling, which is a high pressure air stream. Impingement cooling can be effective at removing a boundary layer of hot "sticky" air that effectively sticks a heat source. In some embodiments, a stack can be configured to have an inlet/outlet pressure ratio of 0.54. In some embodiments, a stack can be configured to provide a pulsed air stream, with pulses delivered approximately every 1.6 seconds. A stack generally requires at least two pressurized air sources fluidly linked in series, however, more (e.g., 1-10) may be used. Each pressurized air source can add 5 psi of pressure to the air that provided to its inlet. For example, a downstream pressurized air source can be provided with air at 5 psi by an upstream pressurized air source, and thus provide 10 psi of air. Generally, the number of pressurized air sources is only limited by air flow, that is, at a certain point air resistance will simply become too great so as to prevent air movement within the stack.

Figure 5A:
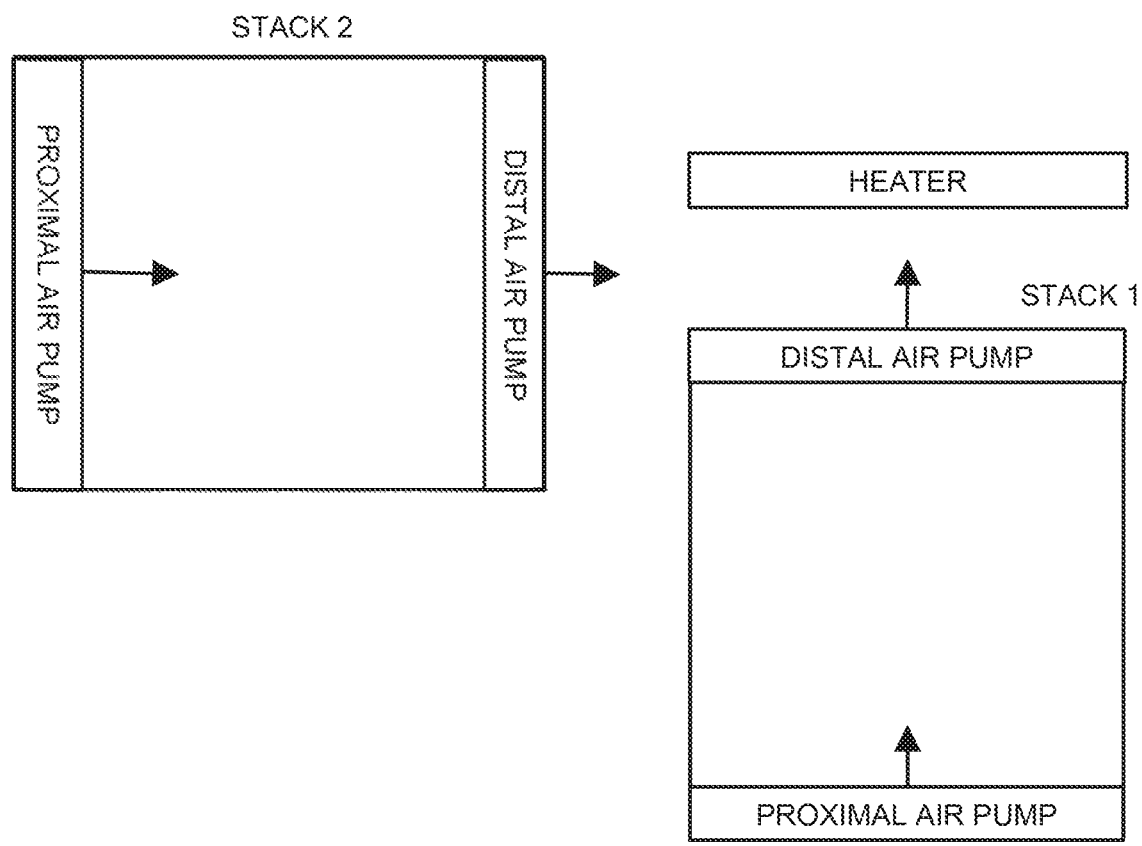
FIGS. 5A-5F are a various schematically diagrams of arrangements of pluralities of linked pressurized air sources, according to some embodiments of the invention.
Figure 5B:
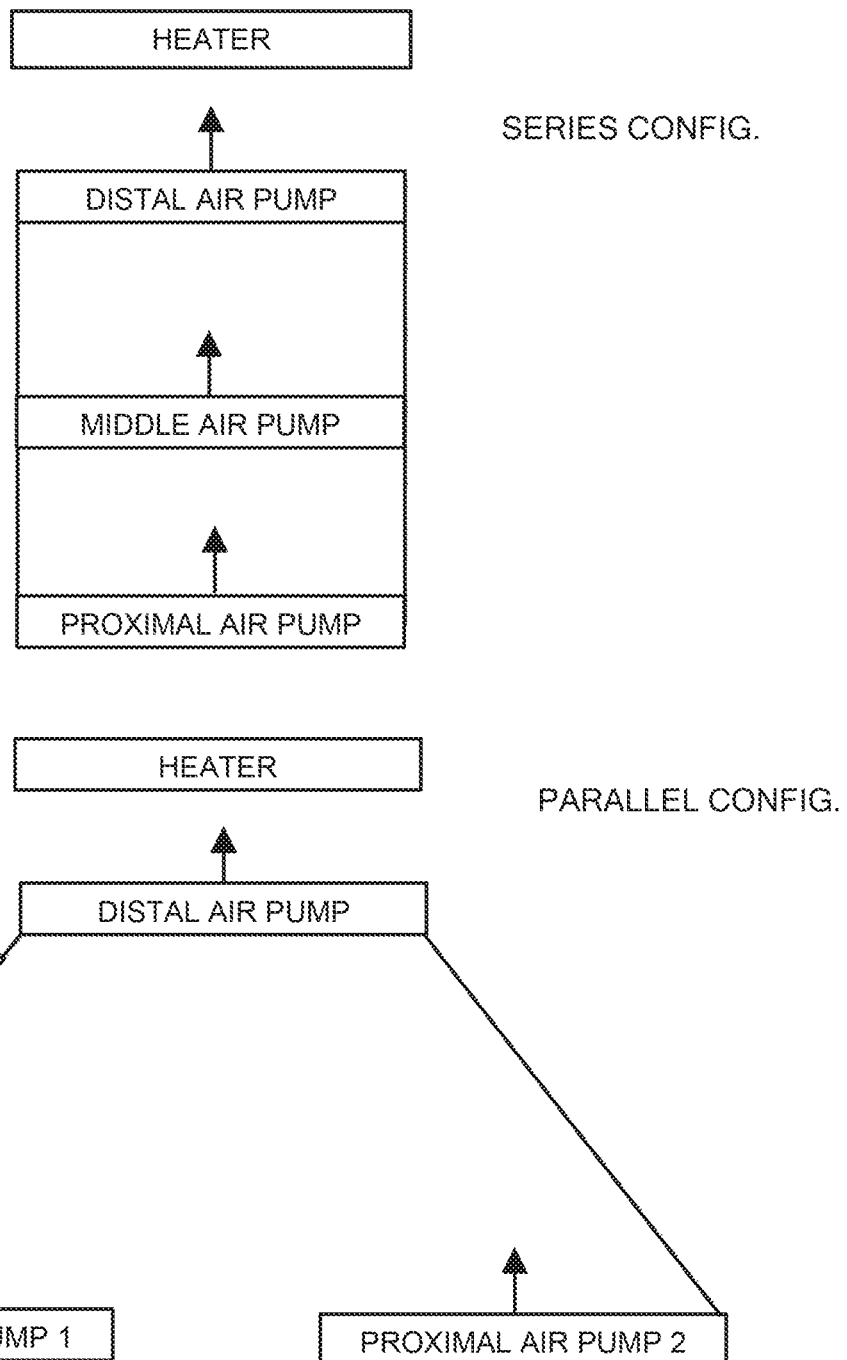
Figure 5C:
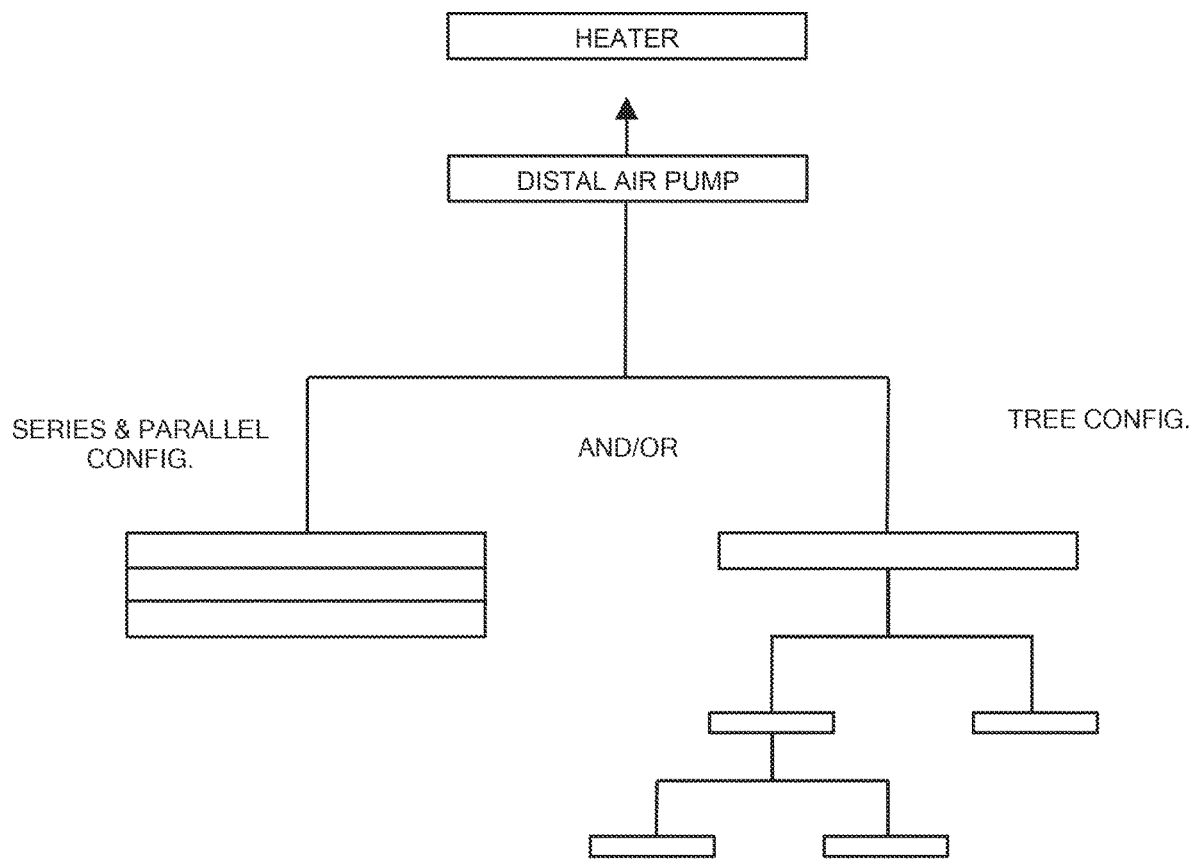
Figure 5D:
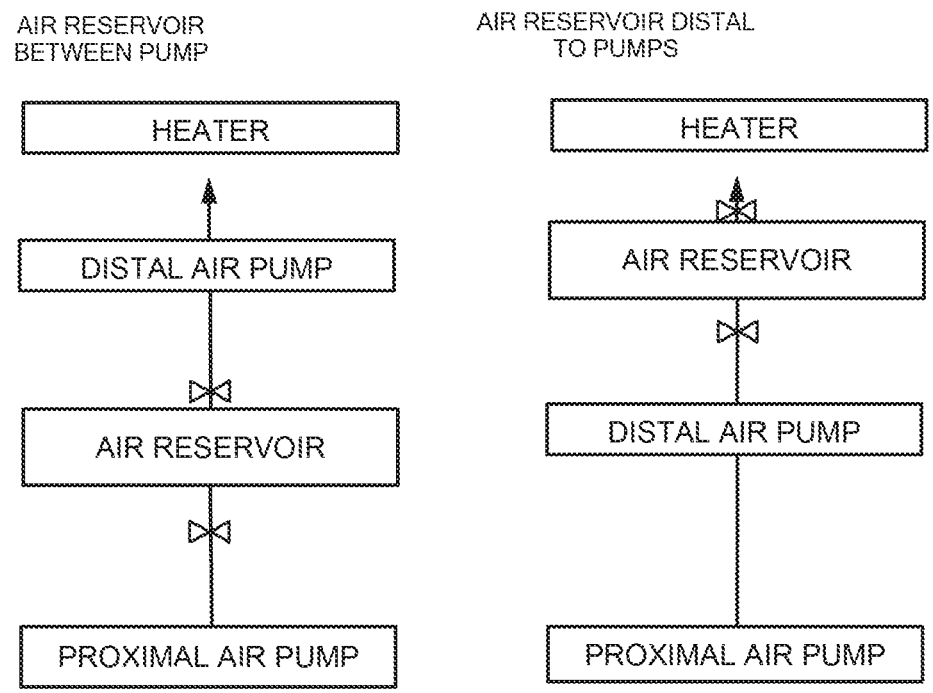
Figure 5D:
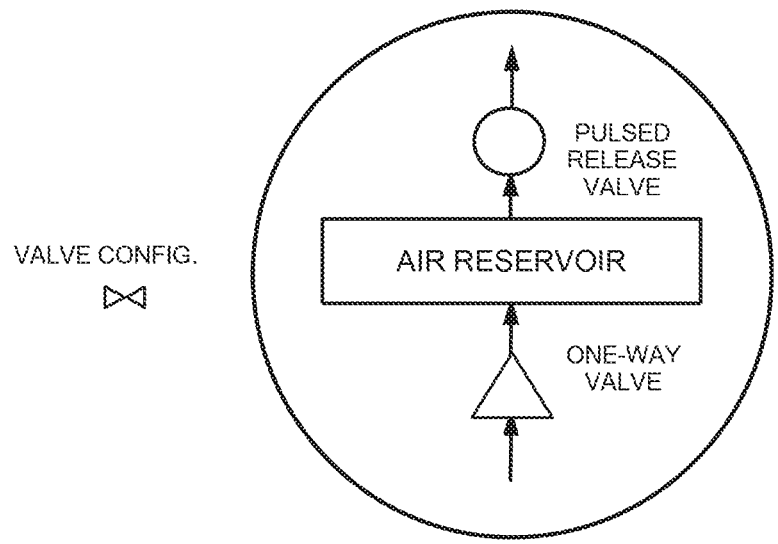
Figure 5E:
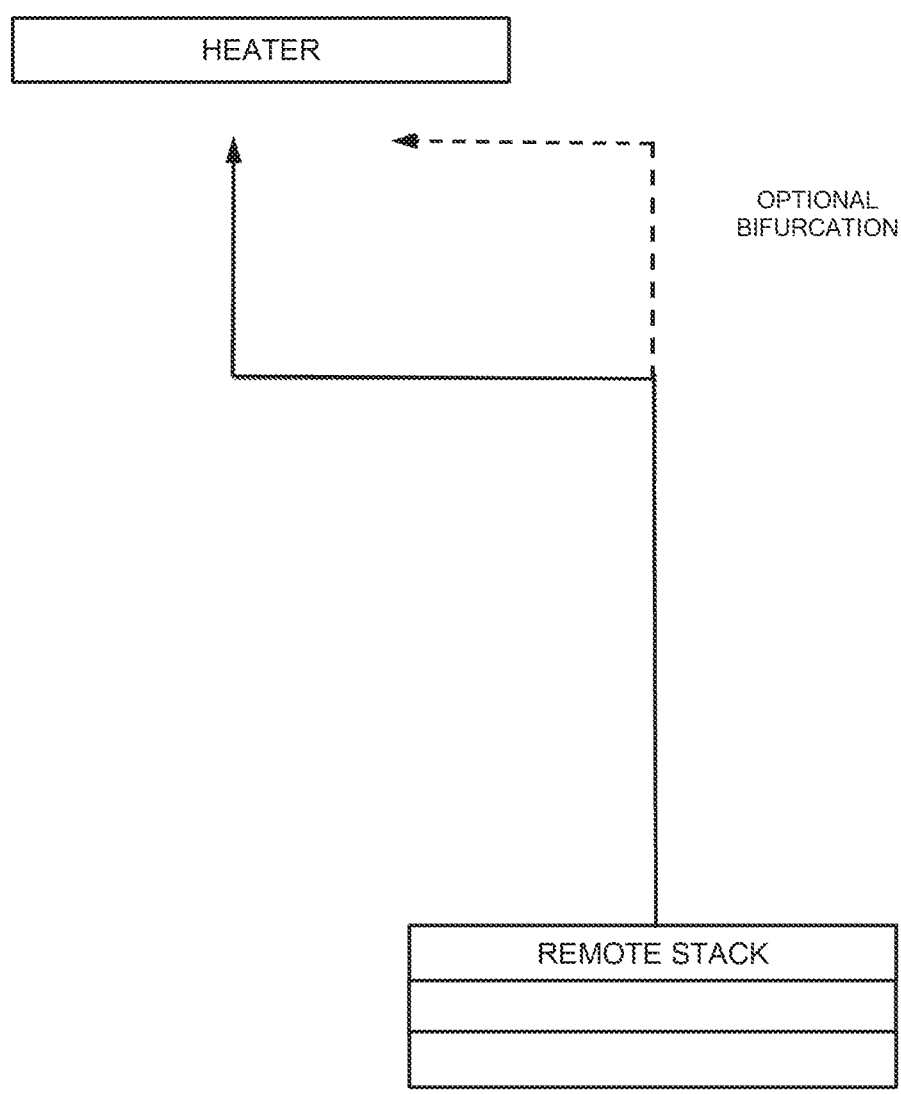

In FIG. 5A a first and second stack are arranged to laterally and transversely direct air at a heat source. FIG. 5B shows a stack configuration having more than two linked cooling sources arranged in series. FIG. 5B also shows a stack configuration having a plurality of cooling sources linked in parallel providing air to a single cooling source. FIG. 5C shows a combination of the configurations of FIG. 5B. FIG. 5D shows stack configurations with valves regulating flow into and out of air reservoirs. These valves can be electronically controlled silicon micro valves configured to provide optimal pressure and flow. FIG. 5E shows a remotely located stack configuration which provides air via an air tube to a heat source. The air tube can be bifurcated to provide more than one air flow direction to the heat source.

In some embodiments, a cooling unit can be attached to a pressure reservoir, as shown in FIG. 5B. The cooling unit can be provide a liquid refrigerant to the one or more walls of the pressure reservoir, to cool pressurized air therein. Commercially available CPU cooling units can be implemented in this manner such that the stack can provide impingement cooling at a temperature lower than ambient air temperature.

Figure 5F:
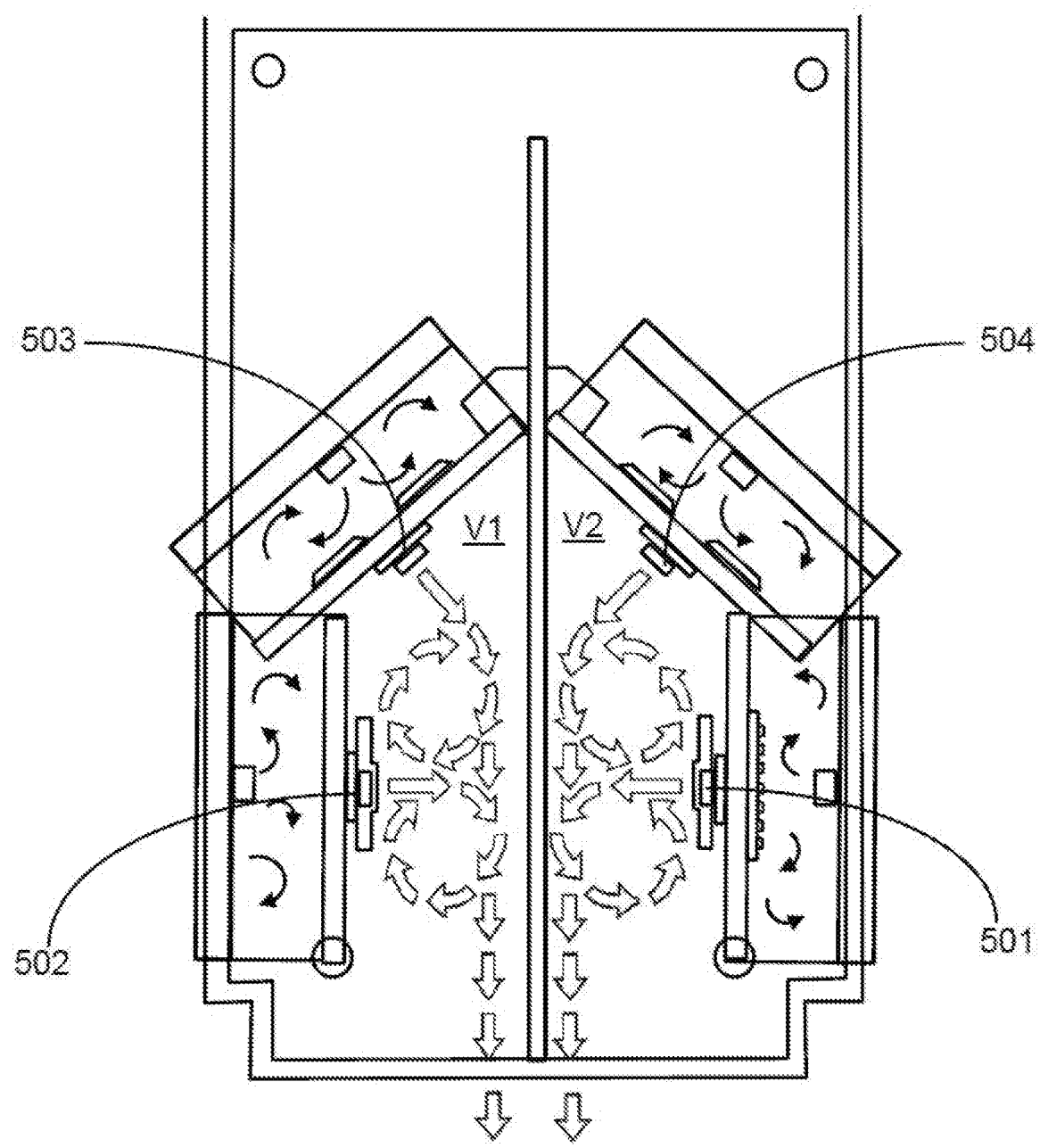

FIG. 5F shows a rearview of a TCD 500 with pluralities of linked pressurized air sources ("stacks")(501, 502, 503, 504) in use. The arrangement of the stacks is in a similar manner to what is shown in FIG. 2C.

While the exemplary embodiments have been described in some detail for clarity of understanding and by way of example, a number of modifications, changes, and adaptations may be implemented. Further, any dimensions mentioned are exemplary guidelines for one skilled in the art, and thus do not represent limitations as to size and/or proportion of the invention.

What is claimed is:

1. A thermal cycling method comprising:
    activating a first heating element and a second heating element, each heating element being positioned adjacent to a biological sample holder;
    directing, using a first air source, a first air stream at the first heating element to transfer heat from the first heating element;
    directing, using a second air source, a second air stream to direct heated air away from the first heating element;
    directing, using a third air source, a third air stream to direct heated air away from the second heating element; and
    directing, using a fourth air source, a fourth air stream at the second heating element to transfer heat from the second heating element.

2. The method of claim 1, wherein the first and second heating elements are positioned on opposed sides of a sample interfacing wall, the sample interfacing wall extending from a mounting surface.

3. The method of claim 2, wherein the air sources each comprise substantially planar housings edge mounted to the mounting surface.

4. The method of claim 2, wherein the first and fourth air streams directly intersect the first and second heating elements.

5. The method of claim 4, wherein the second and third air streams are directed along the sample interfacing wall.

6. The method of claim 4, wherein the second and third air streams are directed away from the sample interfacing wall.

7. The method of claim 4, wherein each air source comprises a planar housing having an internal piezoelectric element mounted to an internal diaphragm.

8. The method of claim 7, wherein directing each air stream comprises powering each piezoelectric element.

9. The method of claim 8, wherein the piezoelectric elements are powered ON and OFF according to a predetermined cooling cycle.

10. The method of claim 9, wherein the heating elements are powered ON and OFF according to a predetermined heating cycle, the ON portion of the heating cycle being out of phase with the ON portion of the cooling cycle.

11. The method of claim 1, further comprising:
    monitoring temperatures of the first and second heating elements.

12. The method of claim 11, wherein the first and second heating elements are activated to provide heat to the biological sample holder according to a predetermined minimum temperature and a predetermined maximum temperature.

13. The method of claim 12, wherein the air sources are controlled to direct air when the biological sample holder reaches the predetermined maximum temperature.

14. The method of claim 13, wherein the air sources are controlled to stop directing air when the biological sample holder reaches the predetermined minimum temperature.

15. The method of claim 1,
    wherein the first air source comprises a first plurality of linked air sources;
    wherein the second air source comprises a second plurality of linked air sources;
    wherein the third air source comprises a third plurality of linked air sources; and wherein the fourth air source comprises a fourth plurality of linked air sources.

16. The method of claim 15, wherein directing the first air stream comprises pumping air from a proximal air source of the first plurality of linked air sources ultimately into a distal air source of the first plurality of linked air sources, or wherein directing the second air stream comprises pumping air from a proximal air source of the second plurality of linked air sources ultimately into a distal air source of the second plurality of linked air sources.

17. The method of claim 15, wherein directing the first air stream comprises pumping air from a proximal air source of the first plurality of linked air sources ultimately into a distal air source of the first plurality of linked air sources, and wherein directing the second air stream comprises pumping air from a proximal air source of the second plurality of linked air sources ultimately into a distal air source of the second plurality of linked air sources.

18. The method of claim 15, wherein directing at least one of the first and second air streams comprises pressurizing an air reservoir fluidly coupled to at least one of the first and second plurality of linked air sources.

19. The method of claim 18, wherein directing at least one of the first and second air streams with the at least one of the first and second plurality of linked air sources further comprises releasing pressurized air from the air reservoir of the respective plurality of linked air sources.

\* \* \* \* \*